(12) United States Patent
Gilson et al.

(10) Patent No.: US 8,038,697 B2
(45) Date of Patent: Oct. 18, 2011

(54) EMBOLIC PROTECTION DEVICE

(75) Inventors: Paul Gilson, Moycullen (IE); Eamon Brady, Elphin (IE); Michael Gilvarry, Ballina (IE)

(73) Assignee: Salviac Limited, Dublin (IE)

( * ) Notice: Subject to any disclaimer, the term of this patent is extended or adjusted under 35 U.S.C. 154(b) by 1223 days.

(21) Appl. No.: 11/529,525

(22) Filed: Sep. 29, 2006

(65) Prior Publication Data

US 2007/0060945 A1 Mar. 15, 2007

Related U.S. Application Data

(63) Continuation of application No. 10/689,846, filed on Oct. 22, 2003, now abandoned, which is a continuation of application No. 09/986,064, filed on Nov. 7, 2001, now Pat. No. 6,726,701, which is a continuation of application No. PCT/IE00/00055, filed on May 8, 2000.

(30) Foreign Application Priority Data

May 7, 1999 (WO) .................. PCT/IE99/00033
May 7, 1999 (WO) .................. PCT/IE99/00036

(51) Int. Cl.
*A61M 29/00* (2006.01)
(52) U.S. Cl. ..................................... 606/200
(58) Field of Classification Search .............. 606/113, 606/114, 127, 159, 200
See application file for complete search history.

(56) References Cited

U.S. PATENT DOCUMENTS

| | | | | | |
|---|---|---|---|---|---|
| 5,800,525 | A | * | 9/1998 | Bachinski et al. | 623/1.1 |
| 5,814,064 | A | * | 9/1998 | Daniel et al. | 606/200 |
| 6,102,917 | A | * | 8/2000 | Maitland et al. | 606/200 |
| 6,171,327 | B1 | * | 1/2001 | Daniel et al. | 606/200 |
| 6,315,794 | B1 | * | 11/2001 | Richter | 623/1.34 |
| 6,540,722 | B1 | * | 4/2003 | Boyle et al. | 606/200 |

* cited by examiner

*Primary Examiner* — Kevin T Truong
(74) *Attorney, Agent, or Firm* — Sughrue Mion, PLLC; Jonathan Feuchtwang

(57) ABSTRACT

A collapsible filter element for a transcatheter embolic protection device, the filter element comprises a collapsible filter body of polymeric material which is movable between a collapsed stored position for movement through a vascular system and an expanded position for extension across a blood vessel such that blood passing through the blood vessel is delivered through the filer element. A proximal inlet portion of the filter body has one or more inlet openings sized to allow blood and embolic material enter the filter body. A distal outlet portion of the filter body has a plurality of generally circular outlet openings sized to allow through-passage of blood, but to retain embolic material within the filter body. The distal outlet portion of the filter body in the region of the outlet openings has means for reducing shear stress on blood passing through the outlet openings. The shear stress reducing means includes lead-in and lead-out radiussed portions of the filter body leading to the outlet holes. The porosity of the distal portion of the filter body decreases towards the distal end. A blind portion extends for at least 5% of the length of the body. Preferably there are between 200 and 300 outlet opening with an average diameter of approximately 150 microns.

26 Claims, 21 Drawing Sheets

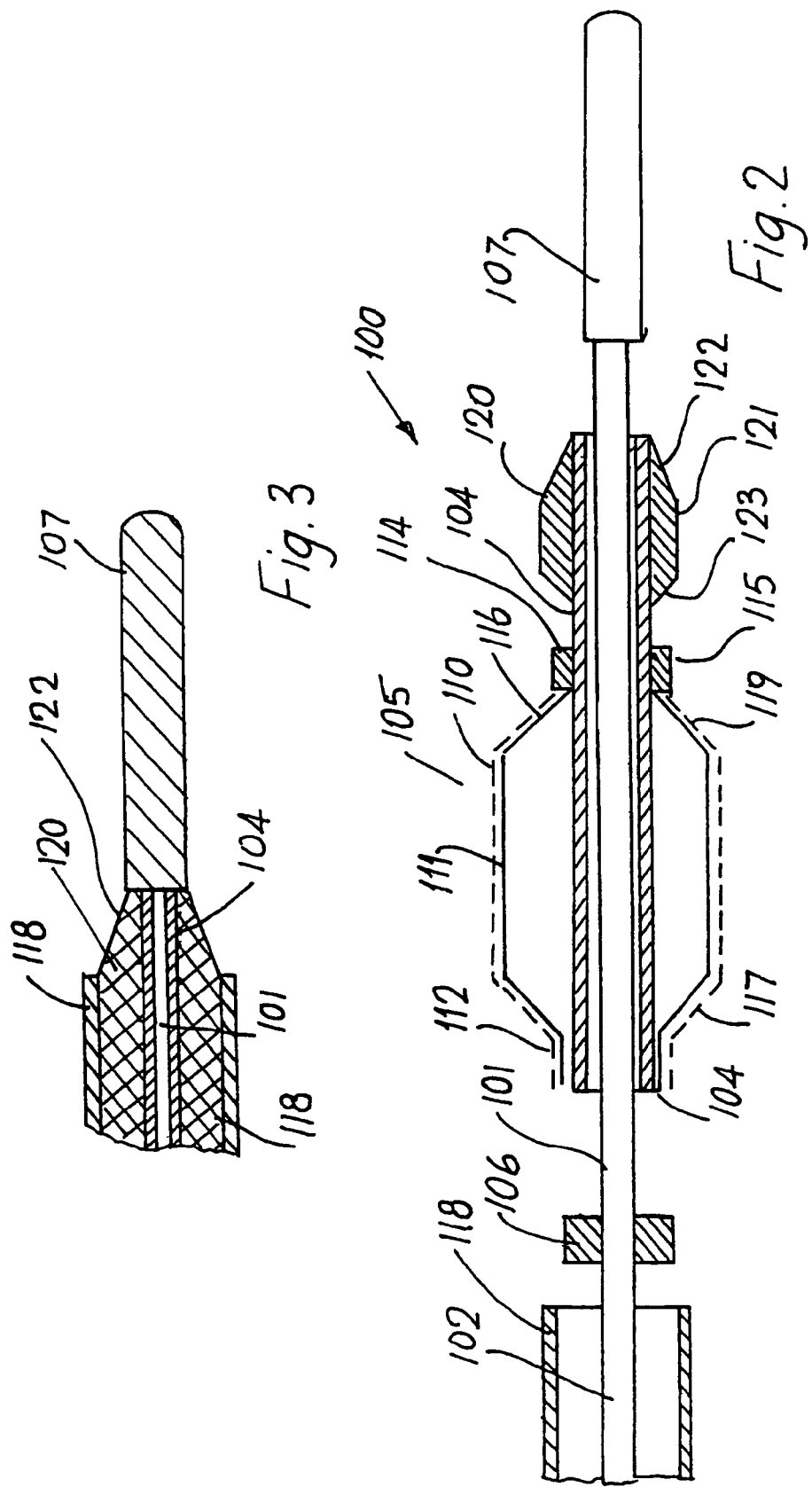

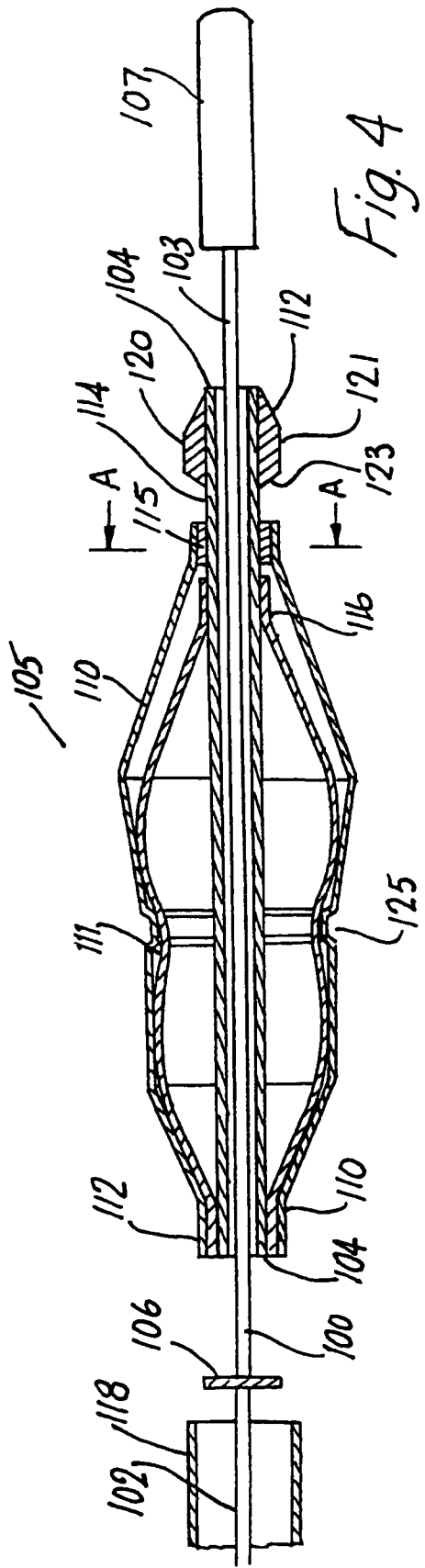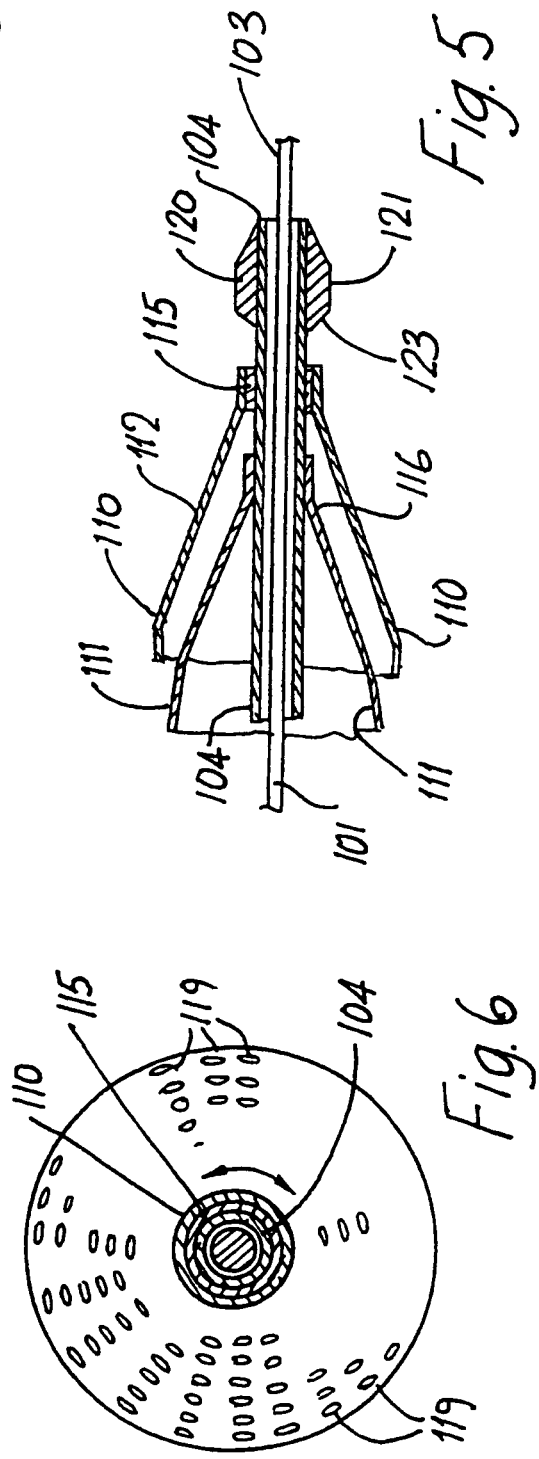
Fig. 4
Fig. 5
Fig. 6

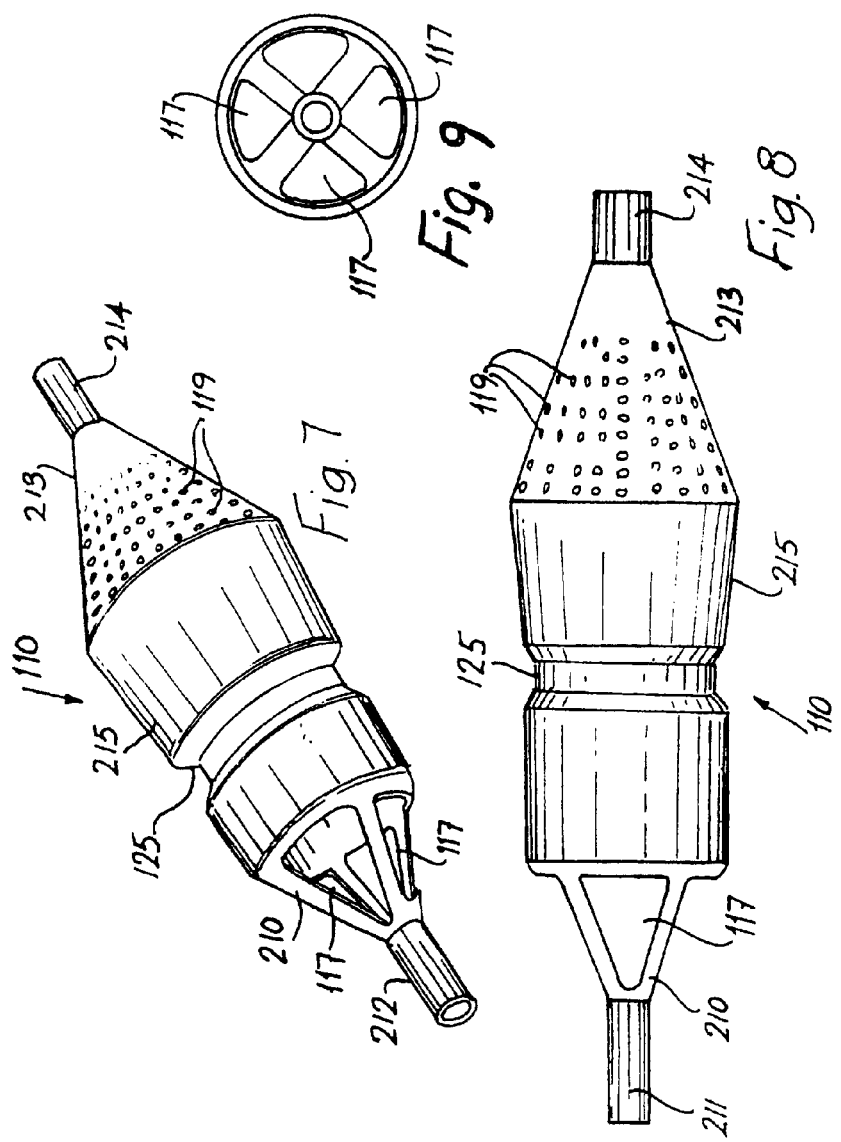

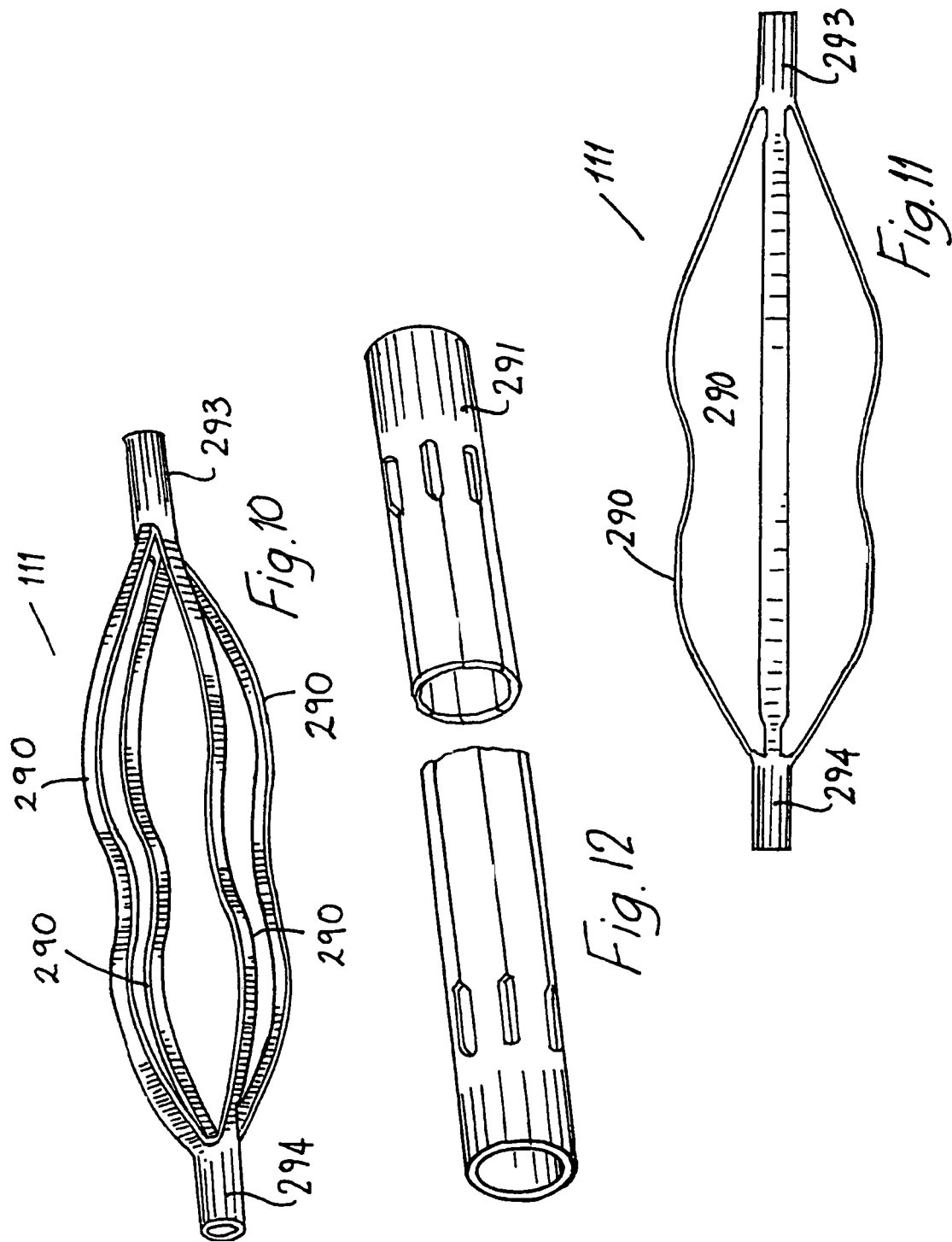

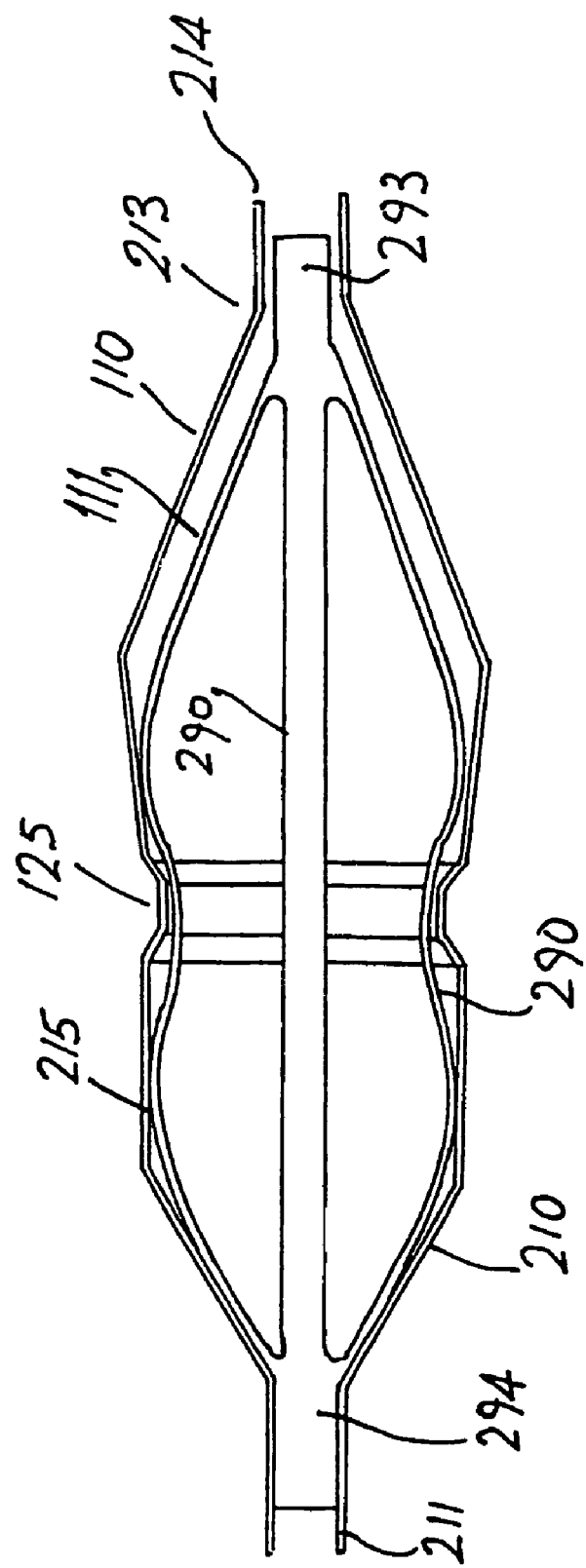

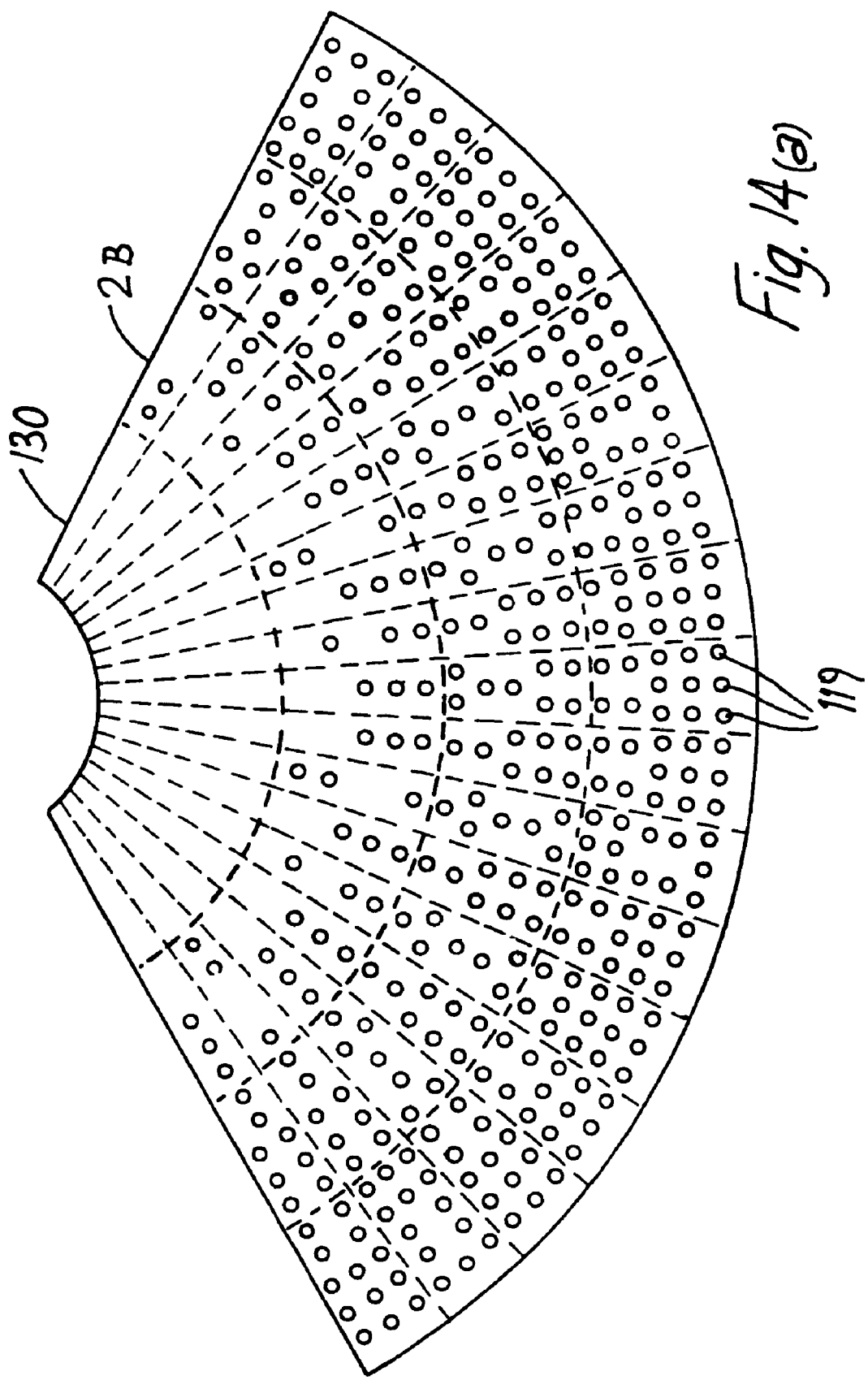

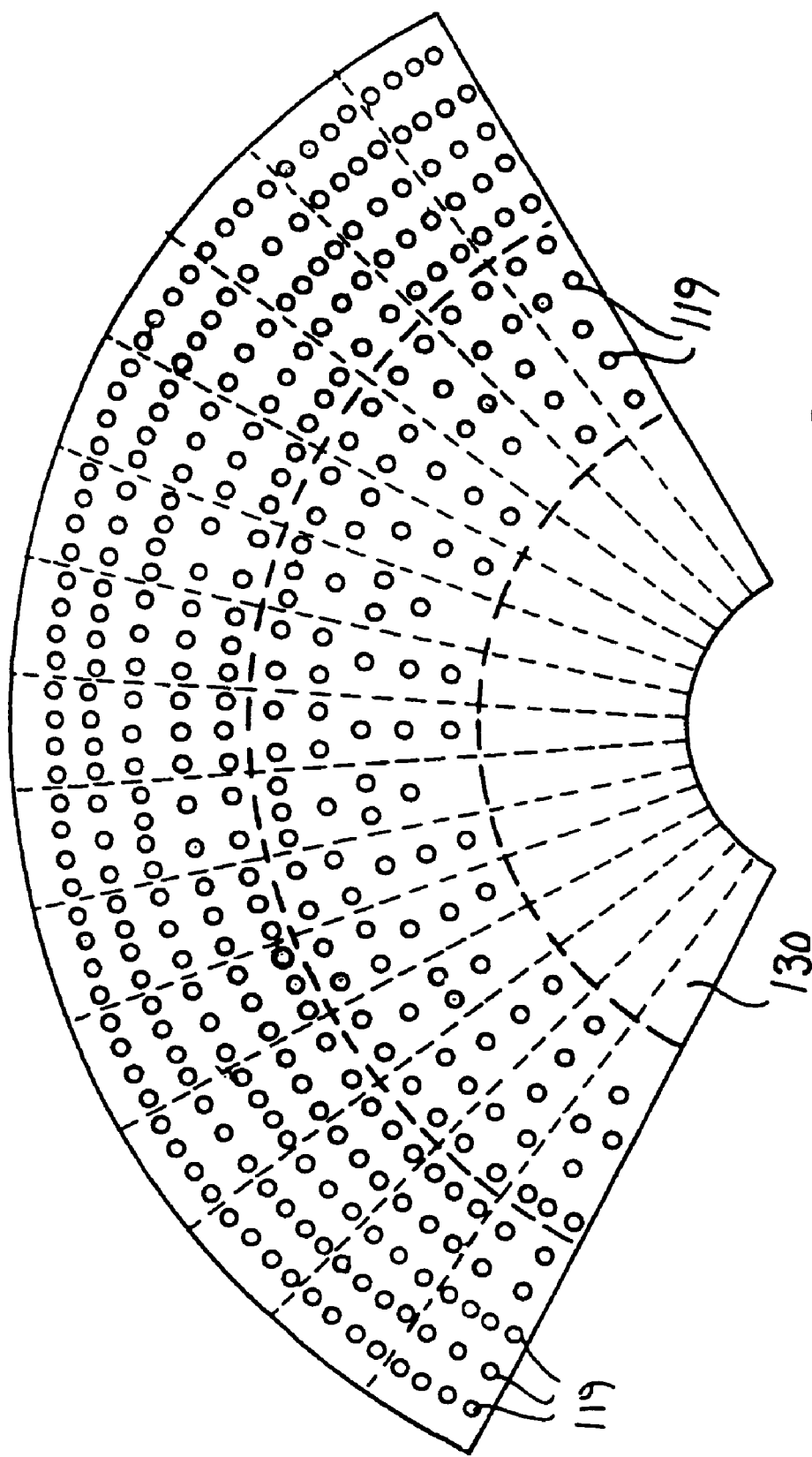

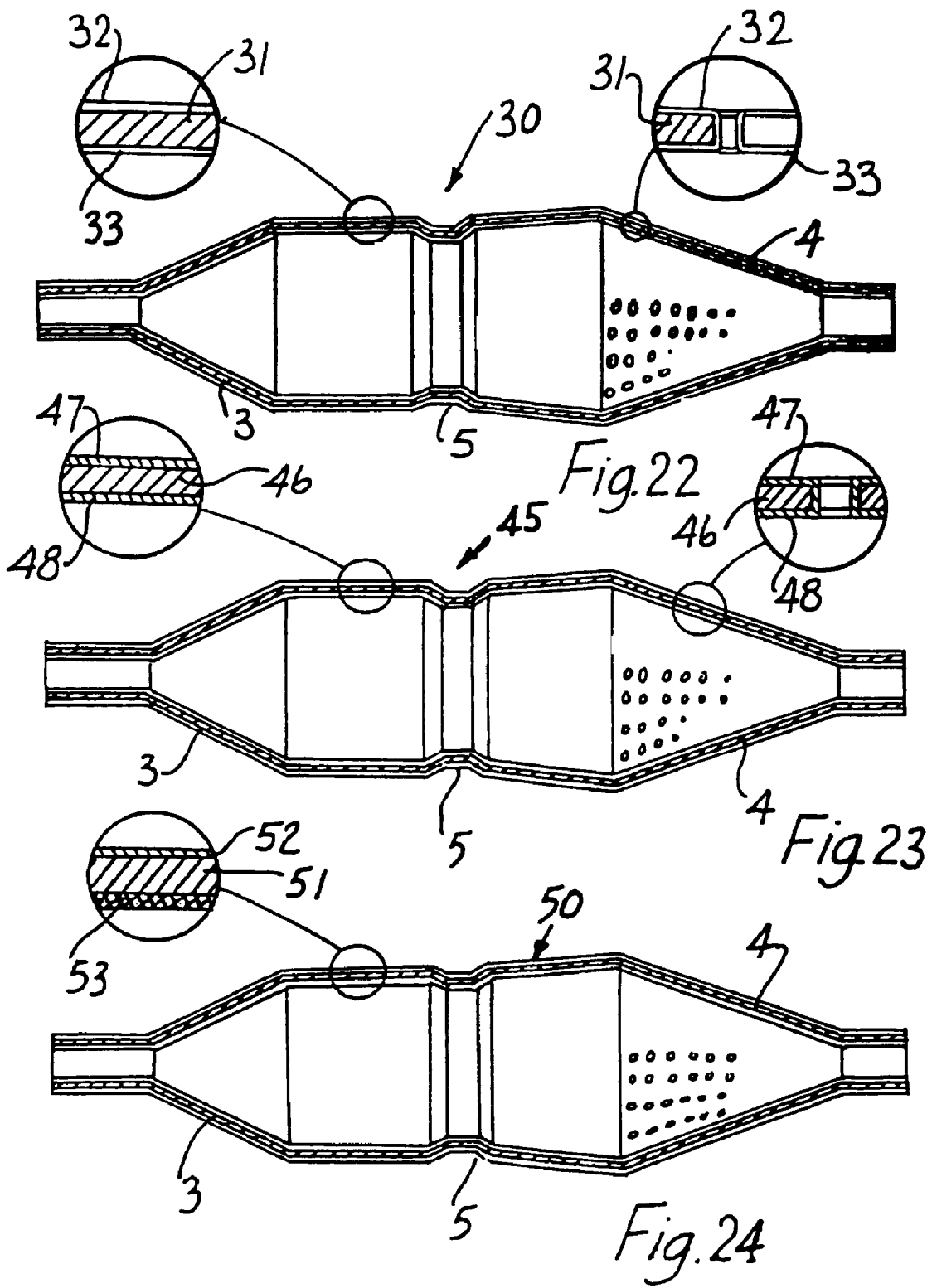

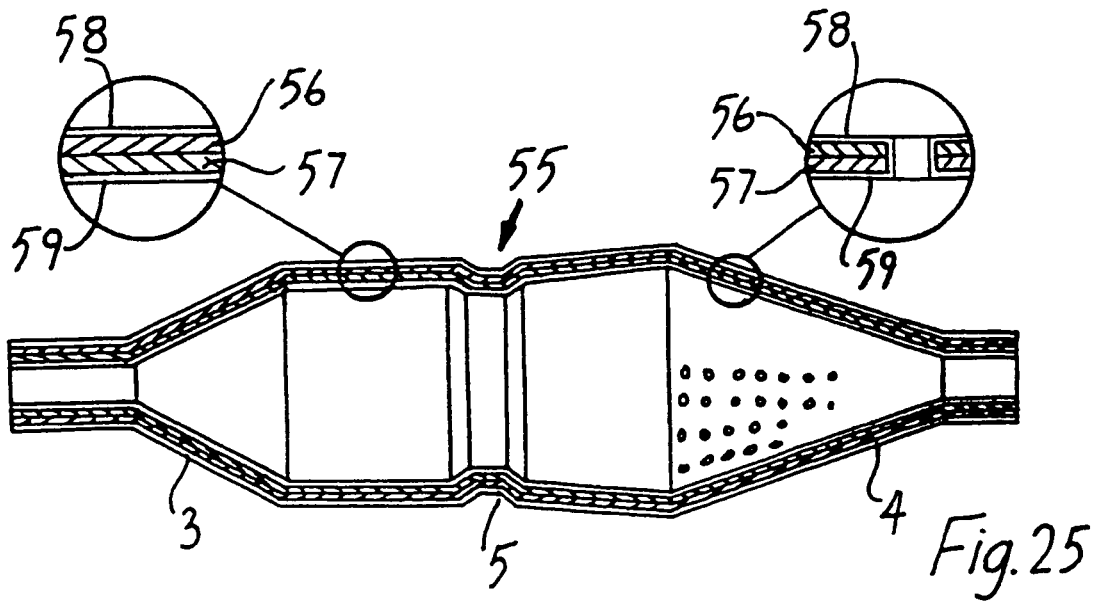
Fig. 25
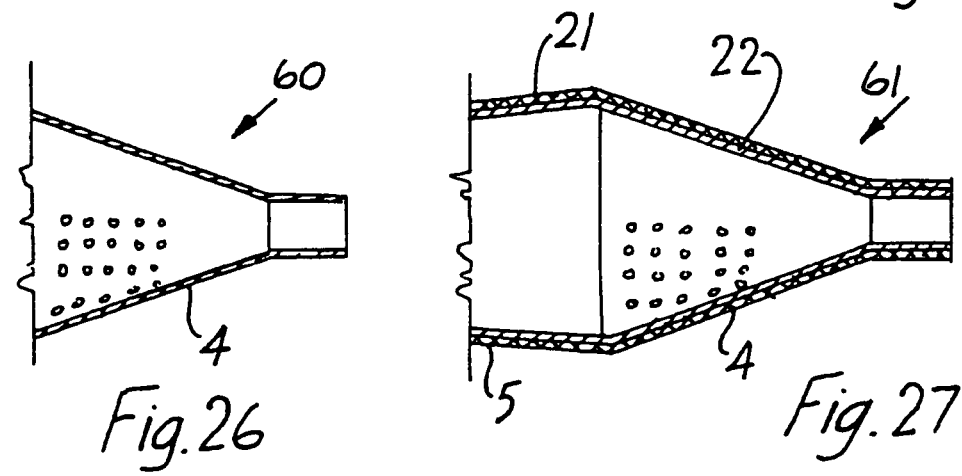
Fig. 26
Fig. 27
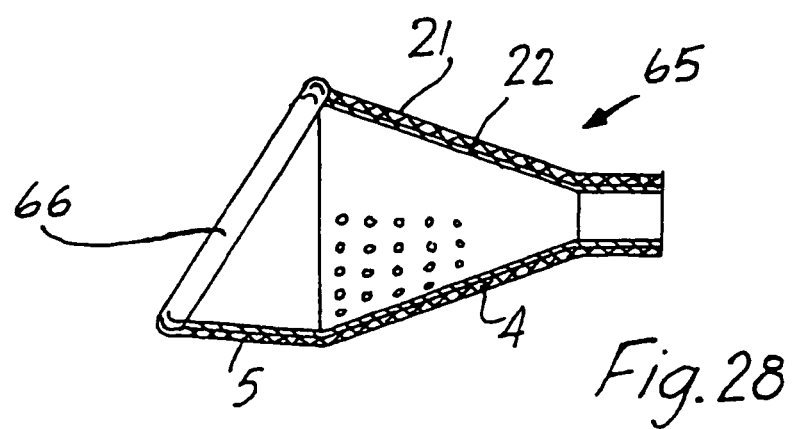
Fig. 28

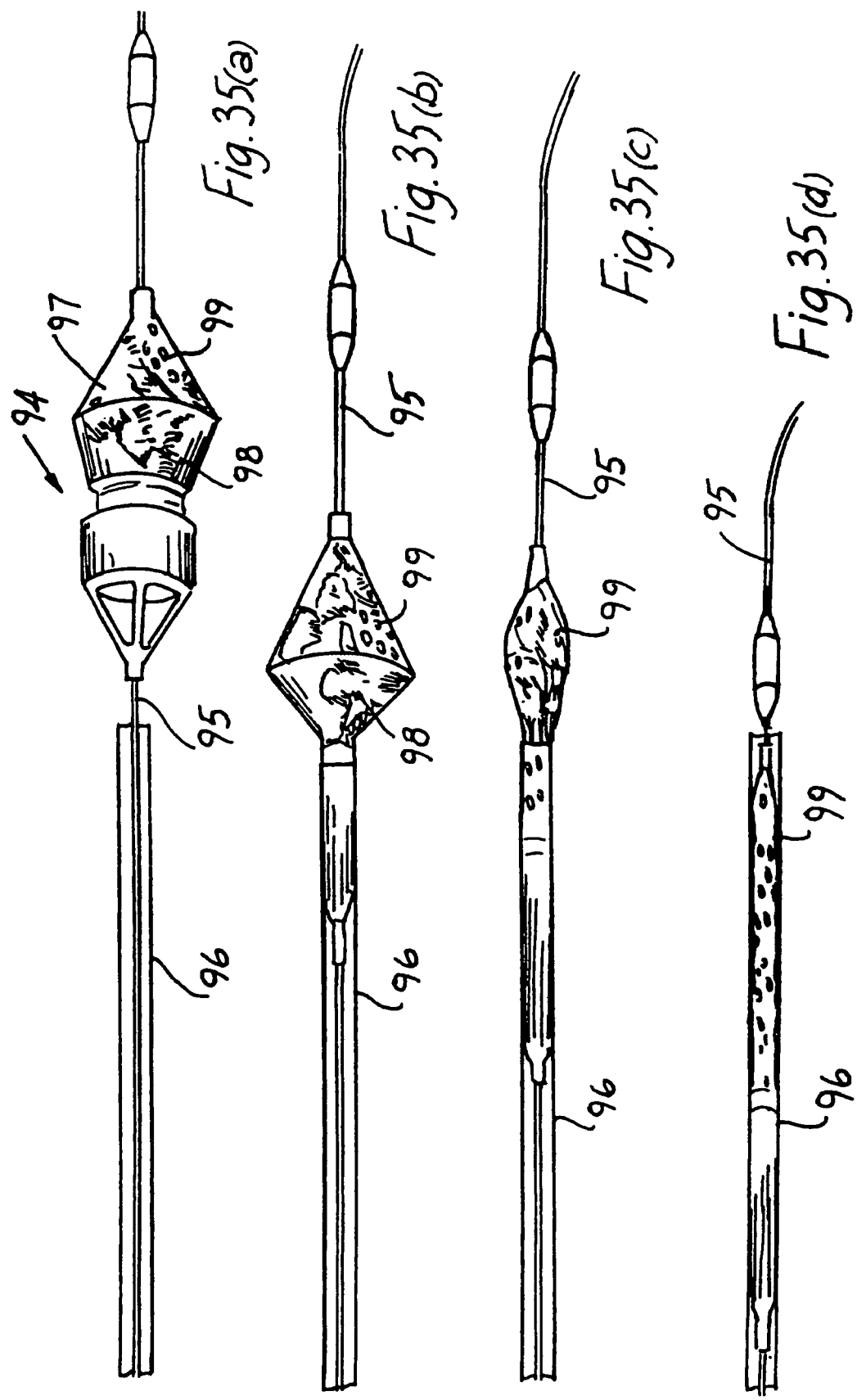

EMBOLIC PROTECTION DEVICE

This is a request for a Continuation Application of prior application Ser. No. 10/689,846 filed Oct. 22, 2003 now abandoned, which is a Continuation of application Ser. No. 09/986,064 (now U.S. Pat. No. 6,726,701), filed Nov. 7, 2001, which is a continuation of PCT/IE00/00055 filed May 8, 2000, which claims benefit of priority from Irish Patent Applications Nos. PCT/IE99/00033 and PCT/IE99/00036, filed May 7, 1999. The entire disclosures of the prior applications, application Ser. Nos. 10/689,846; 09/986,064; and PCT/IE00/00055 are considered part of the disclosure of the accompanying continuation application and are hereby incorporated by reference.

INTRODUCTION

The term "STROKE" is used to describe a medical event whereby blood supply to the brain or specific areas of the brain is restricted or blocked to the extent that the supply is inadequate to provide the required flow of oxygenated blood to maintain function. The brain will be impaired either temporarily or permanently, with the patient experiencing a loss of function such as sight, speech or control of limbs. There are two distinct types of stroke, haemorrhagic and embolic. This invention addresses embolic stroke.

Medical literature describes caroitid artery disease as a significant source of embolic material. Typically, an atherosclerotic plaque builds up in the carotid arteries. The nature of the plaque varies considerably, but in a significant number of cases pieces of the plaque can break away and flow distally and block bloodflow to specific areas of the brain and cause neurological impairment. Treatment of the disease is classically by way of surgical carotid endarterectomy whereby, the carotid artery is cut and the plaque is physically removed from the vessel. The procedure has broad acceptance with neurological complication rates quoted as being low, somewhere in the order of 6% although claims vary widely on this.

Not all patients are candidates for surgery. A number of reasons may exist such that the patients could not tolerate surgical intervention. In these cases and an increasing number of candidates that are surgical candidates are being treated using transcatheter techniques. In this case, the evolving approach uses devices inserted in the femoral artery and manipulated to the site of the stenosis. A balloon angioplasty catheter is inflated to open the artery and an intravascular stent is sometimes deployed at the site of the stenosis. The action of these devices as with surgery can dislodge embolic material which will flow with the arterial blood and if large enough, eventually block a blood vessel and cause a stroke.

It is known to permanently implant a filter in human vasculature to catch embolic material. It is also known to use a removable filter for this purpose. Such removable filters typically comprise umbrella type filters comprising a filter membrane supported on a collapsible frame on a guidewire for movement of the filter membrane between a collapsed position against the guidewire and a laterally extending position occluding a vessel. Examples of such filters are shown in U.S. Pat. No. 4,723,549, U.S. Pat. No. 5,053,008, U.S. Pat. No. 5,108,419, WO97/17100 and WO 98/33443. Various deployment and/or collapsing arrangements are provided for the umbrella filter. However, as the filter collapses, the captured embolic material tends to be squeezed outwardly towards an open end of the filter and pieces of embolic material may escape from the filter with potentially catastrophic results. More usually, the filter umbrella is collapsed against the guidewire before removal through a catheter or the like. Again, as the filter membrane is collapsed, it will tend to squeeze out the embolic material. Further, the umbrella filter is generally fixed to the guidewire and any inadvertent movement of the guidewire during an interventional procedure can dislodge the filter.

The insertion of such known filters in the human vasculature which comprises very small diameter blood vessels may result in inappropriate haemodynamics which can exacerbate damage to the flowing blood and may result in haemolysis.

This invention is therefore directed towards providing an embolic protection device which will overcome these major problems.

STATEMENTS OF INVENTION

According to the invention there is provided a collapsible filter element for a transcatheter embolic protection device, the filter element comprising:
  a collapsible filter body which is movable between a collapsed stored position for movement through a vascular system and an expanded position for extension across a blood vessel such that blood passing through the blood vessel is delivered through the filter element;
  a proximal inlet portion of the filter body having one or more inlet openings sized to allow blood and embolic material enter the filter body;
  a distal outlet portion of the filter body having a plurality of outlet openings sized to allow through-passage of blood, but to retain embolic material within the filter body;
  the distal outlet portion of the filter body in the region of the outlet openings having means for reducing shear stress on blood passing through the outlet openings.

In a preferred embodiment of the invention the shear stress reducing means includes lead-in radiussed portions of the filter body leading to the outlet holes.

In a particular embodiment of the invention the shear stress reducing means includes lead-out radiussed portions of the filter body leading from the outlet holes.

Most preferably the outlet-holes are generally circular.

In another preferred embodiment of the invention the proximal inlet portion of the filter body in the region of the inlet openings has means for reducing shear stress on blood passing through the inlet openings. Preferably the shear stress reducing means includes lead-in radiussed portions of the filter body leading to the inlet holes. Ideally, the shear stress reducing means includes lead-out radiussed portions of the filter body leading from the inlet holes.

In a particularly preferred embodiment the filter is of a polymeric material. Preferably the filter body defines a three dimensional matrix. Most preferably, the filter body is of a resilient elastomeric material. The filter body may be of a polyurethane elastomer. Most preferably the filter body is of a polycarbonate urethane material.

In an especially preferred embodiment of the invention the filter body is covered with a hydrophilic coating, the openings being provided in the coating.

Preferably the filter is of a polymeric material and the raduissed portions are formed by solvent polishing of the polymeric material.

In a preferred embodiment the porosity of the distal portion of the filter body decreases towards the distal end of the filter. Ideally, the overall porosity of the distal portion of the filter element is from 5% to 40%. Preferably the overall porosity of the distal portion of the filter element is form 8% to 21%.

In a preferred embodiment in the transverse cross sectional areas at longitudinally spaced-apart locations of the distal portion are substantially the same.

Preferably the distal portion is of generally conical shape having a radial dimension which decreases towards a distal end of the filter element.

In one embodiment the distal portion includes a blind section adjacent to the distal end of the filter element. Preferably the blind portion extends longitudinally for at least 5% of the length of the distal portion, ideally for less than 30% of the length of the distal portion.

In a preferred arrangement the number of outlet holes increases towards an outer edge of the distal outlet portion of the filter body.

Most preferably there are between 200 and 1000 outlet openings with an average diameter of between 50 and 200 microns. Ideally, there are between 200 and 300 outlet openings with an average diameter of approximately 150 microns. There may be at least 200 outlet openings with an average diameter of no more than 200 microns.

Preferably there are less than 1000 openings with an average, diameter of at least 50 microns.

In a particularly preferred embodiment the openings are sized such that shear stress imparted to blood flowing through the filter body at physiological flow rates is less than 800 Pa, most preferably less than about 400 Pa and ideally less than about 200 Pa.

The openings are ideally generally circular openings.

In a preferred embodiment said filter body, when in a deployed configuration includes a generally cylindrical intermediate section between said proximal and distal portions. The filter body is generally tapered when in a deployed configuration. Preferably said distal section of said filter body comprises at least a portion of the filter element. Ideally said intermediate section of said filter body comprises at least a portion of the filter element.

In a preferred embodiment the intermediate section of said filter body includes a circumferential groove.

In a particularly preferred embodiment said filter body, when in a deployed configuration is defined by a generally elongated shape, having an intermediate section with an axial dimension and a transverse dimension, the ratio of the axial dimension to the transverse dimension being at least 0.5, ideally at least 1.0.

In one embodiment of the invention the filter body includes a guidewire lumen extending co-axially of a longitudinal axis of the filter body.

In another aspect the invention provides a collapsible filter element for a transcatheter embolic protection device, the filter element comprising:
  a collapsible filter body which is movable between a collapsed stored position for movement through a vascular system and an expanded position for extension across a blood vessel such that blood passing through the blood vessel is delivered through the filter element, the filter body having a proximal end, a longitudinal axis and a distal end;
  a proximal inlet portion of the filter body having one or more inlet openings sized to allow blood and embolic material enter the filter body;
  a distal outlet portion of the filter body having a plurality of outlet openings sized to allow through-passage of blood, but to retain embolic material within the filter body;
  the porosity of the distal portion of the filter body decreasing towards the distal end of the filter.

In a further aspect the invention provides a collapsible filter element for a transcatheter embolic protection device, the filter element comprising:
  a collapsible filter body which is movable between a collapsed stored position for movement through a vascular system and an expanded position for extension across a blood vessel such that blood passing through the blood vessel is delivered through the filter element;
  a proximal inlet portion of the filter body having one or more inlet openings sized to allow blood and embolic material enter the filter body;
  a distal outlet portion of the filter body having a plurality of outlet openings sized to allow through-passage of blood, but to retain embolic material within the filter body;
  the filter body comprising a membrane of polymeric material;
  wherein there are between 200 and 1000 outlet openings with an average diameter of between 50 and 200 microns.

The invention also provides a collapsible filter element for a transcatheter embolic protection device, the filter element comprising:
  a collapsible filter body which is movable between a collapsed stored position for movement through a vascular system and an expanded position for extension across a blood vessel such that blood passing through the blood vessel is delivered through the filter element;
  a proximal inlet portion of the filter body having one or more inlet openings sized to allow blood and embolic material enter the filter body;
  a distal outlet portion of the filter body having a plurality of outlet openings sized to allow through-passage of blood, but to retain embolic material within the filter body;
  the filter body comprising a membrane of polymeric material;
wherein the openings are sized such that shear stress imparted to blood flowing through the filter body at physiological flow rates is less than 800 Pa, preferably less than about 400 Pa.

In a further aspect the invention provides a collapsible filter element for a transcatheter embolic protection device, the filter element comprising:
  a collapsible filter body which is movable between a collapsed stored position for movement through a vascular system and an expanded position for extension across a blood vessel such that blood passing through the blood vessel is delivered through the filter element;
  the filter body having a longitudinal axis a proximal inlet portion, a distal outlet portion and an intermediate section extending between the proximal portion and the distal portion;
  a proximal inlet portion of the filter body having one or more inlet openings sized to allow blood and embolic material enter the filter body;
  a distal outlet portion of the filter body having a plurality of outlet openings sized to allow through-passage of blood, but to retain embolic material within the filter body;
  the filter body having a guidewire lumen co-axial with the longitudinal axis;
  wherein in a deployed configuration the intermediate section is generally cylindrical with an axial dimension and a transverse dimension, the ratio of the axial dimension to the transverse dimension being at least 0.5, preferably at least 1.0.

In yet another aspect the invention provides a transcatheter embolic protection device including:
  a delivery system comprising:
    a tubular member having a longitudinal axis, distal and proximal portions, said distal portion of the tubular member being removably advanceable into the vasculature of a patient;

a medical guidewire longitudinally axially movable in said tubular member and having distal and proximal portions;

and a filter element of any aspect of the invention the filter body having;

a first collapsed, insertion and withdrawal configuration an a second expanded, deployed configuration;

a proximal inlet section and a distal outlet section, said proximal inlet section including inlet openings which are operable to admit body fluid when the filter body is in the second expanded configuration;

a plurality of outlet openings disposed on at least a portion of the filter element adjacent to the distal outlet section;

wherein said filter body is moved between said first and second configurations by displacement of said delivery system.

Preferably the filter body has a collapsible filter frame operably coupled thereto. Said frame may comprise a plurality of support arms having proximal and distal ends. Preferably the arms are formed of an elastic shape memory material.

In preferred embodiment said frame is constructed such that filter body is biased toward said second, deployed configuration.

In one embodiment of the invention said inlet openings are defined at least partially by said arms. Preferably proximal portions of said arms extend generally outwardly and distally from said guidewire when said filter body is in said second, deployed configuration.

In one embodiment distal portions of said arms extend generally outwardly and proximally from said guidewire when said filter body is in said second, deployed configuration.

Preferably the distal portion of the tubular member further includes a pod for receiving therein the filter body when in said first, collapsed configuration. Preferably said filter body is urged into said first, collapsed configuration by said pod when the guidewire is moved proximally.

In one embodiment said guidewire is solid.

In one arrangement said filter body comprises a sleeve slidably disposed on said guidewire. The device may further comprise stops for limiting the range of longitudinal movement of the sleeve on said guidewire. The sleeve may comprise a guidewire member distal to the filter body tapering distally.

BRIEF DESCRIPTION OF THE DRAWINGS

The invention will be more clearly understood from the following description thereof given by way of example only with reference to the accompanying drawings in which:

FIG. 2 is a schematic sectional elevational view of the embolic protection device of FIG. 1;

FIG. 3 is a sectional view of the distal end of the device of FIG. 1 shown in its loaded condition within its delivery catheter;

FIG. 4 is a longitudinal cross sectional view of the device of FIG. 1;

FIG. 5 is a cross sectional view of a distal end of the device of FIG. 1;

FIG. 6 is a view on the line A-A in FIG. 4;

FIG. 7 is a perspective view of a filter body of the device of FIGS. 1 to 6;

FIG. 8 is a side elevational view of the filter body of FIG. 7;

FIG. 9 is a view on a proximal end of the filter body;

FIG. 10 is a perspective view of a support frame;

FIG. 11 is a side elevational view of the support frame;

FIG. 12 is a perspective view illustrating the manufacture of the support frame;

FIG. 13 is a view of the support frame and filter body assembly;

FIGS. 14A to 14E are developed views of the distal end of a filter body illustrating different arrangements of outlet holes for filter sizes 6 mm, 4 mm, 4.5 mm, 5 mm, and 5.5 mm respectively;

FIGS. 20 to 25 are longitudinal cross sectional views of different embodiments of the filter body according to the invention;

FIGS. 26 to 28 are longitudinal cross sectional views of further embodiments of the filter body according to the invention;

FIGS. 35(a) to 35(d) are longitudinal side views of another filter according to the invention in different configurations of use.

DETAILED DESCRIPTION

Figure 1:
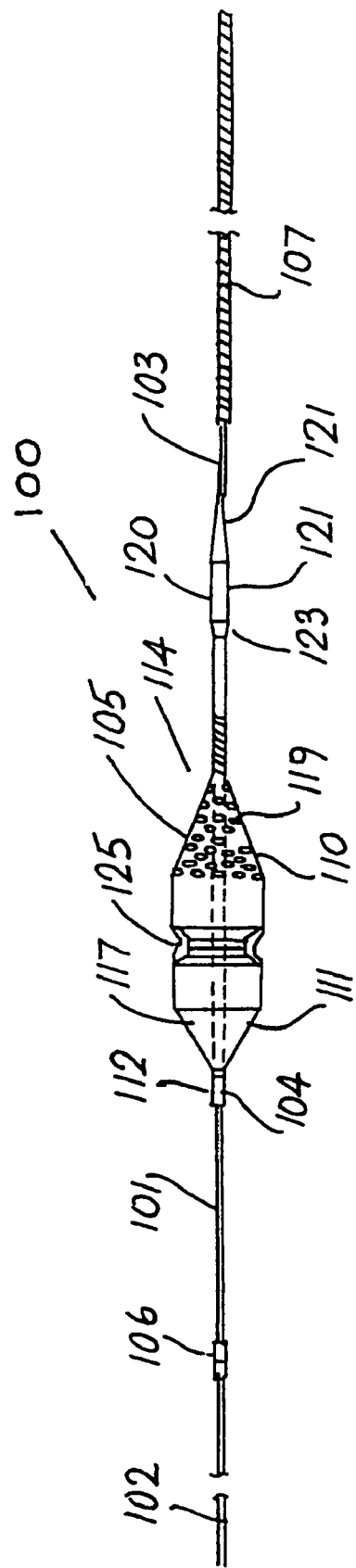
FIG. 1 is partially sectioned elevational view of an embolic protection device according to the invention.

Referring to FIGS. 1 to 13 there is illustrated an embolic protection device as described in our WO-A-9923976 indicated generally by the reference number 100. The device 100 has a guidewire 101 with a proximal end 102 and a distal end 103. A tubular sleeve 104 is slidably mounted on the guidewire 101. A collapsible filter 105 is mounted on the sleeve 104, the filter 105 being movable between a collapsed stored position against the sleeve 104 and an expanded position as shown in the drawings extended outwardly of the sleeve 104 for deployment in a blood vessel.

The sleeve 104 is slidable on the guidewire 101 between a pair of spaced-apart end stops, namely an inner stop 106 and an outer stop which in this case is formed by a spring tip 107 at the distal end 103 of the guidewire 101.

The filter 105 comprises a filter body 110 mounted over a collapsible support frame 111. The filter body 110 is mounted to the sleeve 104 at each end, the body 110 being rigidly attached to a proximal end 112 of the sleeve 104 and the body 110 being attached to a collar 115 which is slidable along a distal end 114 of the sleeve 104. Thus the distal end of the body 110 is longitudinally slidable along the sleeve 104. The support frame 111 is also fixed at the proximal end 112 of the sleeve 104. A distal end 116 of the support frame 111 is not attached to the sleeve 104 and is thus also free to move longitudinally along the sleeve 104 to facilitate collapsing the support frame 111 against the sleeve 104. The support frame 111 is such that it is naturally expanded as shown in the drawings and can be collapsed inwardly against the sleeve 104 for loading in a catheter 118 or the like.

The filter body 110 has large proximal inlet openings 117 and small distal outlet openings 119. The proximal inlet openings 117 allow blood and embolic material to enter the filter body 110, however, the distal outlet openings 119 allow through passage of blood but retain undesired embolic material within the filter body 110.

An olive guide 120 is mounted at a distal end of the sleeve 104 and has a cylindrical central portion 121 with tapered ends 122, 123. The distal end 122 may be an arrowhead configuration for smooth transition between the catheter and olive surfaces. The support frame 111 is shaped to provide a circumferential groove 125 in the filter body 110. If the filter 105 is too large for a vessel, the body 110 may crease and this groove 125 ensures any crease does not propagate along the filter 105.

Enlarged openings are provided at a proximal end of the filter body 110 to allow ingress of blood and embolic material into an interior of the body 110.

Referring in particular to FIGS. 10 to 13 the collapsible support frame 111 has four foldable arms 290 which are collapsed for deployment and upon release extend outwardly to expand the filter body 110.

The support frame 111 can be manufactured from a range of metallic or polymeric components such as a shape memory alloy like nitinol or a shape memory polymer or a shaped stainless steel or metal with similar properties that will recover from the deformation sufficiently to cause the filter body 110 to open.

The support frame 111 may be formed as illustrated in FIG. 12 by machining slots in a tube 291 of shape memory alloy such as nitinol. On machining, the unslotted distal end of the tube 291 forms a distal collar 293 and the unslotted proximal end of the tube 291 forms a proximal collar 294. In use, as described above, the distal collar 293 is slidably movable along the tubular sleeve 104 which in turn is slidably mounted on the guidewire 101 for deployment and retrieval. The proximal collar 294 is fixed relative to the tubular sleeve 104.

To load the filter 105 the sub assembly of the support frame 111 and filter body 110 is pulled back into the catheter 118 to engage the distal stop 107. The support arms 290 are hinged inwardly and the distal collar 293 moves forward along the tubular sleeve 104. As the support arms 290 enter the catheter 118 the filter body 110 stretches as the filter body collar 115 slides along the tubular sleeve 104 proximal to the olive 120. On deployment, the catheter 118 is retracted proximally along the guidewire 101 initially bringing the collapsed filter assembly with it until it engages the proximal stop 106. The catheter sleeve then begins to pull off the filter 105 freeing the support arms 290 to expand and the filter body 110 apposes the vessel wall.

For retrieval, a retrieval catheter is introduced by sliding it over the guidewire 101 until it is positioned at the proximal end of the filter body 110 and support frame 111. Pulling the guidewire 101 will initially engage the distal stop 107 with the filter element and begin to pull it into the retrieval catheter. The initial travel into the retrieval catheter acts to close the proximal openings 117 of the filter element, thus entrapping the embolic load. As the filter 105 continues to be pulled back the filter body 110 and the support frame 111 are enveloped in the retrieval catheter. The collapsed filter 105 may then be removed from the patient.

Conveniently the tip of the catheter which forms a housing or pod for reception of the filter is of an elastic material which can radially expand to accommodate the filter with the captured embolic material. By correct choice of material, the same catheter or pod can be used to deploy and retrieve the filter. For deployment, the elastic material holds the filter in a tightly collapsed position to minimise the size of the catheter tip or pod. Then, when retrieving the filter, the catheter tip or pod is sufficiently elastic to accommodate the extra bulk of the filter due to the embolic material.

Also, the filter is not fast on the guidewire and thus accidental movement of the guidewire is accommodated without unintentionally moving the filter, for example, during exchange of medical devices or when changing catheters.

It will also be noted that the filter according to the invention does not have a sharp outer edge as with many umbrella type filters. Rather, the generally tubular filter shape is more accommodating of the interior walls of blood vessels.

Conveniently also when the filter has been deployed in a blood vessel, the catheter can be removed leaving a bare guidewire proximal to the filter for use with known devices such as balloon catheter and stent devices upstream of the filter.

The outer filter body 110 is preferably of a resilient biocompatible elastomeric material. The material may be a polyurethane based material. There are a series of commercially available polyurethane materials that may be suitable. These are typically based on polyether or polycarbonate or silicone macroglycols together with diisocyanate and a diol or diamine or alkanolamine or water chain extender. Examples of these are described in EP-A-461,375 and U.S. Pat. No. 5,621,065. In addition, polyurethane elastomers manufactured from polycarbonate polyols as described in U.S. Pat. No. 5,254,622 (Szycher) are also suitable.

The filter material may also be a biostable polycarbonate urethane article an example of which may be prepared by reaction of an isocyanate, a chain extender and a polycarbonate copolymer polyol of alkyl carbonates. This material is described in our WO 9924084.

The filter body may be manufactured from a block and cut into a desired shape. The filter may be preferably formed by dipping a rod of desired geometry into a solution of the material which coats the rod. The rod is then dissolved. The final geometry of the filter may be determined in the dipping step or the final geometry may be achieved in a finishing operation. Typically the finishing operations involve processes such as mechanical machining operations, laser machining or chemical machining.

The filter body is of hollow construction and may be formed as described above by dipping a rod in a solution of polymeric material to coat the rod. The rod is then dissolved, leaving a hollow body polymeric material. The rod may be of an acrylic material which is dissolved by a suitable solvent such as acetone.

The polymeric body thus formed is machined to the shape illustrated in FIGS. 1 to 13. The final machined filter body comprises an inlet or proximal portion 210 with a proximal neck 212, and outlet or distal portion 213 with a distal neck 214, and an intermediate portion 215 between the proximal and distal portions.

Alternatively the filter body may be formed by a blow moulding process using a suitably shaped mould. This results in a filter body which has thin walls.

The inlet holes 117 are provided in the proximal portion 210 which allow the blood and embolic material to flow into the filter body. In this case the proximal portion 210 is of generally conical shape to maximise the hole size.

The intermediate portion 215 is also hollow and in this case is of generally cylindrical construction. This is important in ensuring more than simple point contact with the surrounding blood vessel. The cylindrical structure allows the filter body to come into soft contact with the blood vessel to avoid damaging the vessel wall.

The intermediate portion 215 is provided with a radial stiffening means, in this case in the form of a radial strengthening ring or rim 220. The ring 220 provides localised stiffening of the filter body without stiffening the material in contact with the vessel. Such an arrangement provides appropriate structural strength so that line apposition of the filter body to the vessel wall is achieved. It is expected that other geometries of stiffening means will achieve a similar result.

The tubular intermediate portion 215 is also important in maintaining the stability of the filter body in situ to retain captured emboli and to ensure that flow around the filter is minimised. For optimum stability we have found that the ratio of the axial length of the intermediate portion 215 of the filter body to the diameter of the intermediate portion 215 is preferably at least 0.5 and ideally greater than 1.0.

The outlet holes 119 are provided in the distal portion 213 which allow blood to pass and retain embolic material in the filter body.

The purpose of the filter is to remove larger particulate debris from the bloodstream during procedures such as angioplasty. In one case the filter is used to prevent ingress of embolic material to the smaller blood vessels distal to a newly-deployed carotid stent. A known property of the filter is that it will present a resistance to the blood flow. The maximum blood pressure in the arterial system is determined by the muscular action of the heart. The cardiovascular system is a multiple-redundant network designed to supply oxygenated blood to the tissues of the body. The path from the heart through the site of deployment of the filter and back to the heart can be traced through the system. In the absence of the filter this system has a resistance, and the flow through any part of it is determined by the distribution of resistance and by the pressure generated by the heart.

The introduction of the filter adds a resistance on one of the paths in the network, and therefore there will be a reduced blood flow through this part of the circuit. It is reasonable to assume that the flow along the restricted carotid will be inversely proportional to the resistance of this branch of the circuit. For laminar flow in a tube the resistance is independent of the flow rate.

The performance of vascular filters and particularly vascular filters for smaller blood vessels is determined by the relationship between the filter and the media being filtered. Blood is a complex suspension of different cell types that react differently to different stimuli. The defining geometric attributes of the filter structure will establish the filter's resistance to flow in any blood vessel. Ideally, all flow will be through the filter and will be exposed to minimal damage.

All filters that do not have a sealing mechanism to divert flow only through it and will have some element of flow around it. We have configured the filter geometry such that flow through the filter is maximised and flow around the filter is minimised. Pressure drop across the face of the filter when related to the pressure drop through the alternate pathway will determine the filter efficiency.

Related to the pressure drop, is the shear stress experienced by the blood elements. Red cells have an ability to deform under the influence of shear stresses. At low stresses (physiological) this deformation is recoverable. Additionally, a percentage of the red cell population is fragile and will fragment at low shear stress even in patients with "healthy" cell populations. While the body can deal with the rupture and fragmentation of small numbers of red blood cells, gross red blood cell damage are likely to be problematic clinically.

Consideration must be given to the effects of the shear stresses, both the intensity and duration, on the constituent blood particles and the haemostatic mechanisms. It is the effects on the red blood cells and platelets that are of primary importance.

Shear stresses can cause red cell destruction which is more pronounced in patients with red cell disorders, such as sickle cell disease. Haemolysis can lead to anaemia, which can impede oxygen transportation around the body, and in extreme cases causes damage to the kidneys, but this would be unlikely given the relatively short duration of deployment of vascular filters.

More importantly though, shear stress also causes damage to the platelets themselves. Platelets play a key role in haemostasis and help orchestrate the complex cascade of events that lead to blood clot formation. The damage to the platelets causes communication chemicals to be released, and these "activate" other platelets in the vicinity. Once activated, the platelets swell and their surfaces become sticky, and this causes them to aggregate together and on available surfaces to form a "clump". The released chemicals attract and activate other platelets in the area such that the clump grows in size. Fibrous proteins are also created and together a blood clot (thrombus) is formed. Depending on its size and position, the thrombus may occlude some of the holes in a vascular filter. It is also possible for the thrombus to become detached, particularly on removal of the device, and float freely away downstream to become an embolus. Should the embolus be large enough to become trapped in a narrow arterial vessel further along the system, flow in that vessel would be compromised and this could lead directly to stroke. Platelet aggregation occurs most effectively in stagnant and re-circulating flow regions.

It is also known that activated platelets can coat foreign bodies in the blood, such as intravasculature catheters. The foreign material surface then becomes sticky and therefore a site for further aggregation. This in turn could affect the local geometry of the device and the local flow characteristics.

Shear may be expressed as follows:

Wall shear stress: $\tau = 4\mu Q/\pi R^3$

Figure 18:
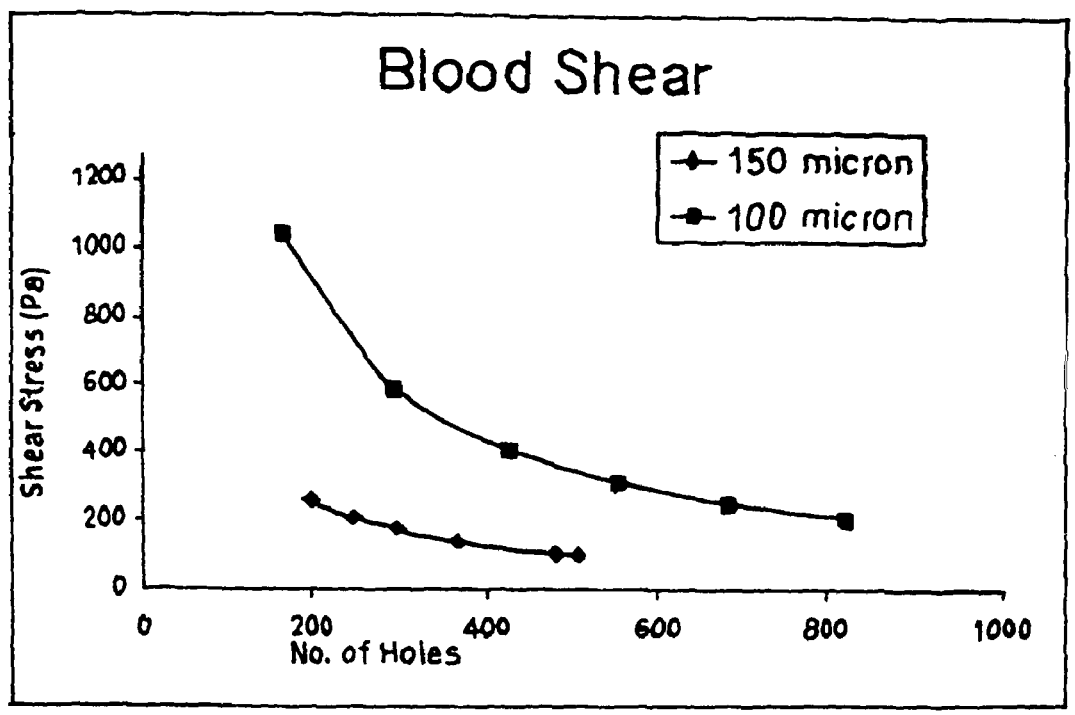
FIG. 18 is a graph of shear stress with outlet hole size and hole number.

Where
  $\mu$ is the blood viscosity
  Q is the mass flow rate
  R is the vessel radius In FIG. 18 we show the relationship under specific flow conditions in a stated diameter of vessel. This plot assumes a Newtonian fluid, equal flow rate through each hole, a flow rate of 270 ml/min and a 4 mm blood vessel.

The relationship shows that as hole size decreases, then the required number of holes increases significantly.

This representation of shear is a good general representation however, local conditions at the filter pores can have significant impact on the shear with flow irregularities generating the possibility of shear levels increasing by an order of magnitude. The location of the maximum shear stress is at the edges of the filter holes at their downstream side. The filter element of the invention has local radii and the filter entrance and exit holes to minimise the shear stress levels. Holes may be drilled using mechanical drilling or laser cutting. However, these processes can produce dimensionally repeatable holes but will impart surface conditions that are not suitable for small vessel filtration. Any fraying of edges due to mechanical cutting will certainly cause flow disruptions and form sites for platelet aggregation. Similarly laser cutting due to its local intense heating and vaporisation of the substrate will lead to pitting, surface inclusions, rough edges and surface imperfections.

In the invention the holes are post processed to modify the surfaces and to radius the edges. A preferred embodiment of the filter element is manufactured using a medial grade polyurethane such as Chronoflex™ supplied by Cardiotech Inc. The filter holes are post-processed by solvent polishing using acetone or other suitable solvent.

Figure 17A:
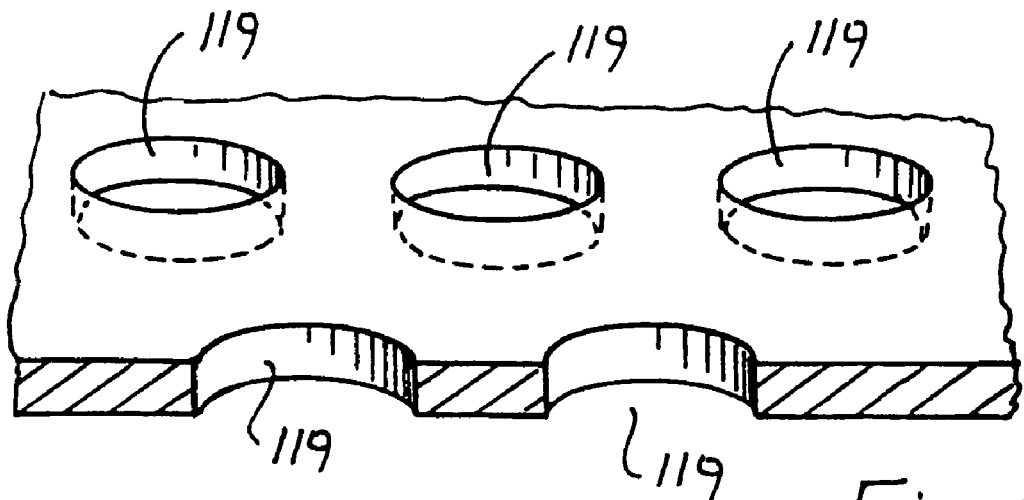
FIGS. 17(a) and 17(b) are perspective partially cut-away cross sectional views of a filter body before and after solvent polishing respectively.
Figure 17B:
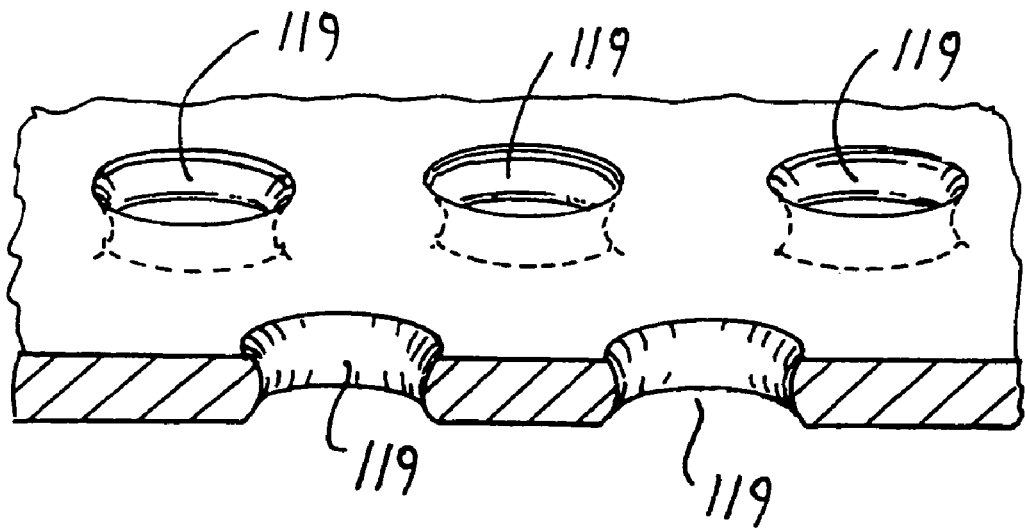

Referring in particular to FIG. 17(a) there is illustrated a section of a polymeric filter body with a number of machined outlet holes 119. After solvent polishing the hoes are surface treated providing radiused lead-in and lead-out portions.

Solvent polishing of the membrane is achieved by softening the material in the surface layers of the membrane such that a local reflow process is facilitated. This reflow is achieved using one of two classes of solvent.

Solvents that have an ability to dissolve the polymer.
Solvents that have an ability to swell the polymer.

The process for the first class of solvents involves exposing the membrane to a limited amount of the solvent. This is achieved by dipping the membrane in the solvent for a short time or exposing the membrane to concentrated vapours of the solvent for a time. The solvent is absorbed into the surface layers and they become solubilised. The solubilised surface layers act like a viscous liquid and they adopt configurations of lowest surface energy. The lowest energy configuration for a liquid is a sphere. The sharp edges and corners become rounded by the solubilisation of the surface. The solvent is dried to reveal a smooth solvent polished surface.

Swelling solvents act slightly differently in that they cannot dissolve the material. However their ability to swell the material allows similar reflow processes to occur. The key difference is that the membrane is immersed in the solvent for a longer period of time, preferably in excess of 30 minutes. The solvent swelling process is most effective when the membrane material is a two phase polymer such as a polyuerthane or a PEBAX, as the solvent can be selected to match either phase.

Solvents will dissolve polymers when their solubility parameters are similar. Solvents will swell a polymer when their solubility parameters are slightly different. Preferably the swelling solvent swells the material by less than 30%. Above this level the solvent should be considered dissolving solvent.

Having reduced the local shear stresses as described above, it is then desirable to minimise the propensity for the activated platelets to adhere to the filter substrate. The more preferred embodiment of filter is one where the polished polymeric surface is combined with a coating on the substrate.

The swelling of the polymer matrix reduces residual stresses that may have developed during the coated core drying or lasering processes. During the lasering process, the material in the immediate proximity of the lasered holes will have been exposed to heat. This heat will disrupt hard segment crystallites and they will reform to lower order metastable structures or be completely dissolved in the soft phase. The heat will also induce the soft segments to contract, however, the re-arrangement of the hard segments imposes new restrictions on the recovery of the soft segments to an equilibrium (relaxed) state. Thus, on removal of the heat source (laser), the morphology of the block copolymer will have changed, in the sense that the new configurations of the hard segments and soft segments will have been frozen in. After lasering, the holes have sharp and well-defined geometries. After exposing the coated material to the solvent, the solvent uncoils the soft segment chains and disassociates low ordered hard segment that are dissolved in the soft segment phase, so on removal of the solvent, the polymer matrix dries in a more relaxed state. In so doing, the sharp, well-defined walls of the lasered holes are transformed to a more contoured relaxed state.

Such applicable solvents for this application, but not limited to, are 2-propanone, methyl ethyl ketone or trichloroethylene.

The solvent characteristics are described as follows at room temperature:

The solvent is organic, colourless and in a liquid state.
The overall solubility parameter of the solvent is quoted between 16 to 26 Mpa$^{0.5}$.
The solvent is polar and is also capable of hydrogen bond interactions.
On partitioning the overall solubility parameter of the solvent into dispersion, polar and hydrogen bonding components, the hydrogen bonding value (in its own solution) is quoted between 3 Mpa$^{0.5}$ to 8.5 Mpa$^{0.5}$
The solvent is infinitely misible in water.
The solvent is aprotic (proton acceptor) towards the formation of hydrogen bonding between it and the polymer.

We have found that the optimum average diameter of the outlet holes in the polymeric membrane is from 100 to 200 microns, ideally approximately 150microns. The number of holes in the distal portion 213 is from 200 to 500, ideally about 300. This hole size and number of holes minimises shear levels by reducing localised flow rates. Thus, we have found that shear can be maintained below 800, preferably below 500 and ideally below 200 Pa at a blood flow rate of up to 270 ml/min in a 4 mm blood vessel. Ideally the holes are circular holes.

We have found that by maintaining blood shear below 800, preferably below 500 and ideally below 200 Pa, the filter provides appropriate haemodynamics to minimise turbulence and inappropriate shear stress on native arteries and veins. Damage to flowing blood such as haemolysis which involves the destruction of red blood cells by rupture of the cell envelope and release of contained haemoglobin is avoided. The outlet hole size and number of holes is optimised in order to capture embolic material, to allow the embolic material to be entrapped in the filter body and to be withdrawn through a delivery device such as a delivery catheter on collapsing of the filter body.

Shearing of red blood and damage to platelets during filtration is a problem easily solved in extra-corporeal circuits by providing large filter areas with consequent low flow rates through individual pores controlled to flow rates such that the shear is maintained in ranges that are below known threshold levels with clinical relevance.

However, as shear stress increases in inverse proportion to the cube of the radius, small blood vessels do not provide space in which to control shear levels by reducing localised flow rates. At flow rates up to 270 ml/min in a 4 mm blood vessel we have found that we can maintain shear at levels below 200 Pa with 150 micron holes.

We have also found that the porosity of the distal end of the filter membrane and the arrangement of outlet holes is important in optimising capture of embolic material without adversely effecting blood shear characteristics and the material properties of the filter body which allow it to be collapsed for delivery, expanded for deployment and collapsed for retrieval.

Figure 14B:
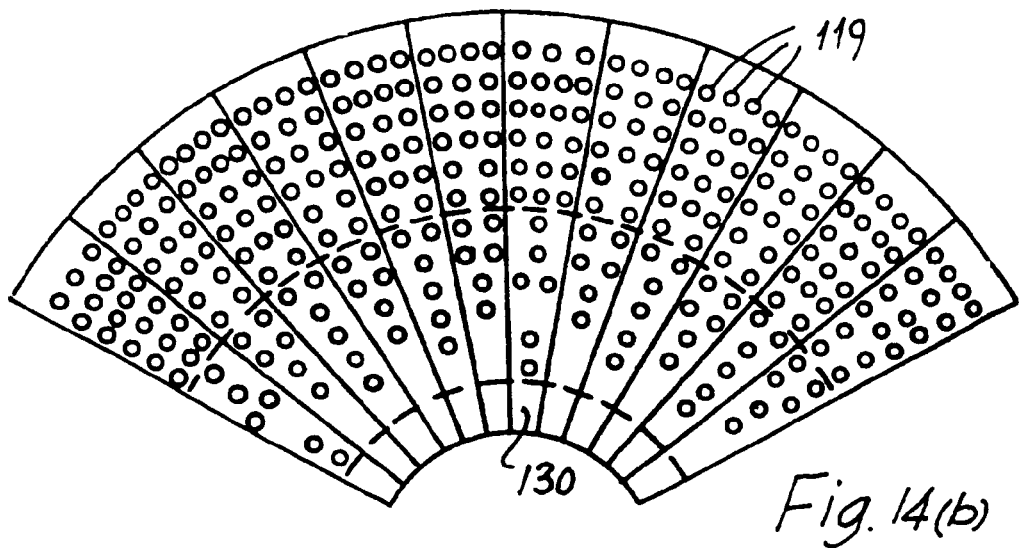
Figure 14C:
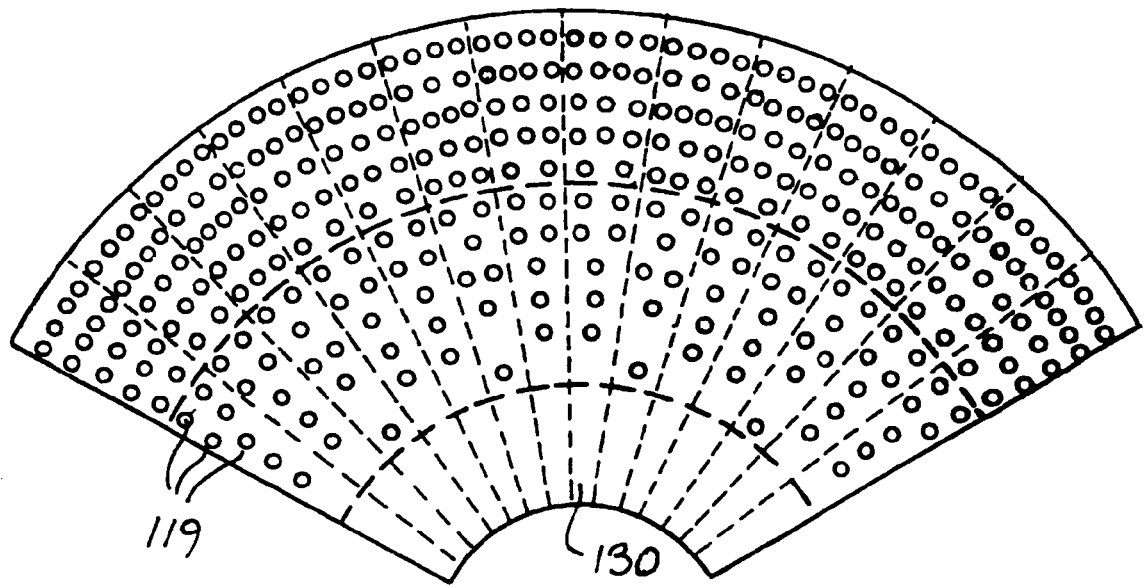
Figure 14E:
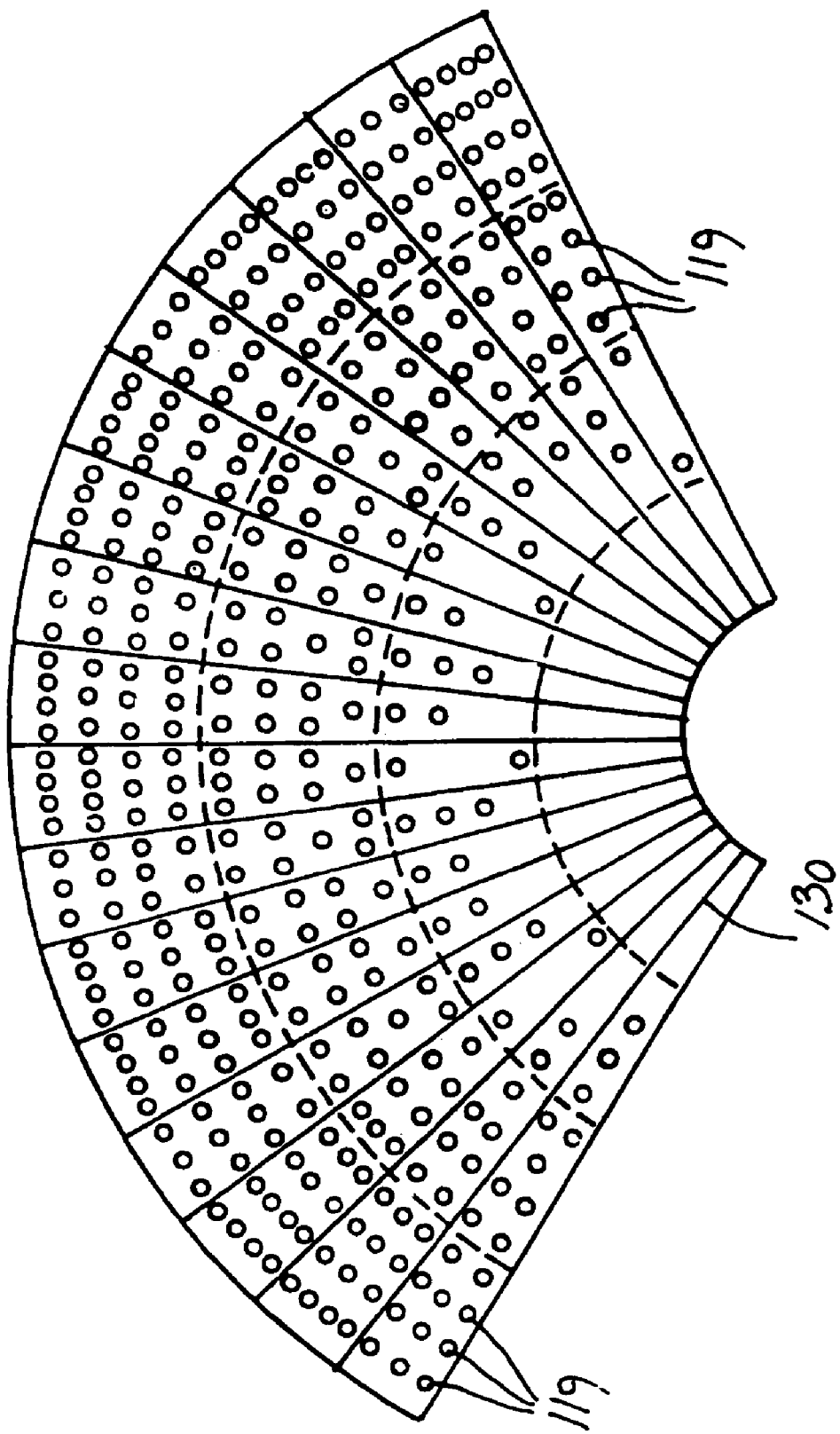
Figure 15:
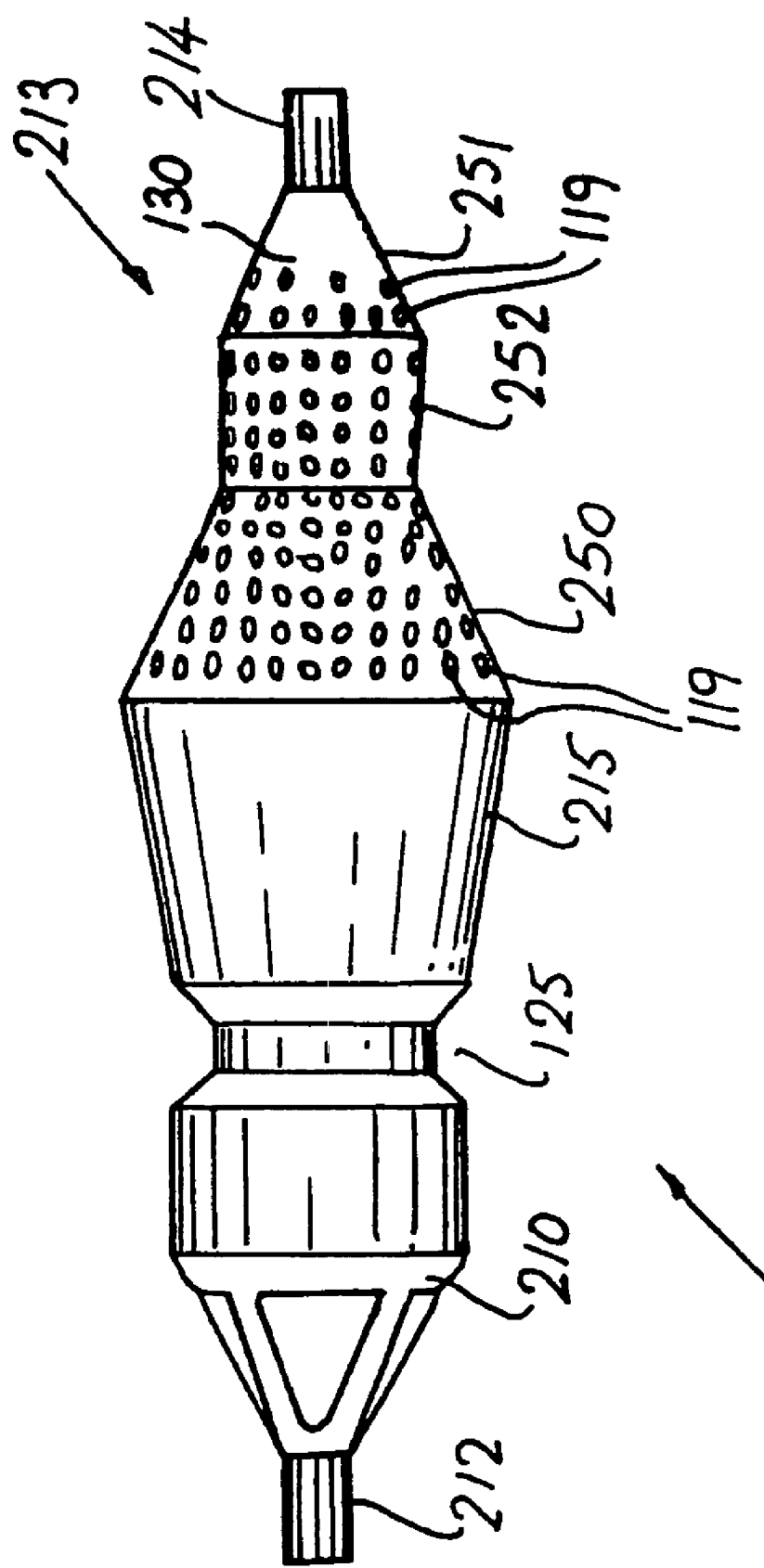
FIG. 15 is a side elevational view of another filter body of the invention.
Figure 16:
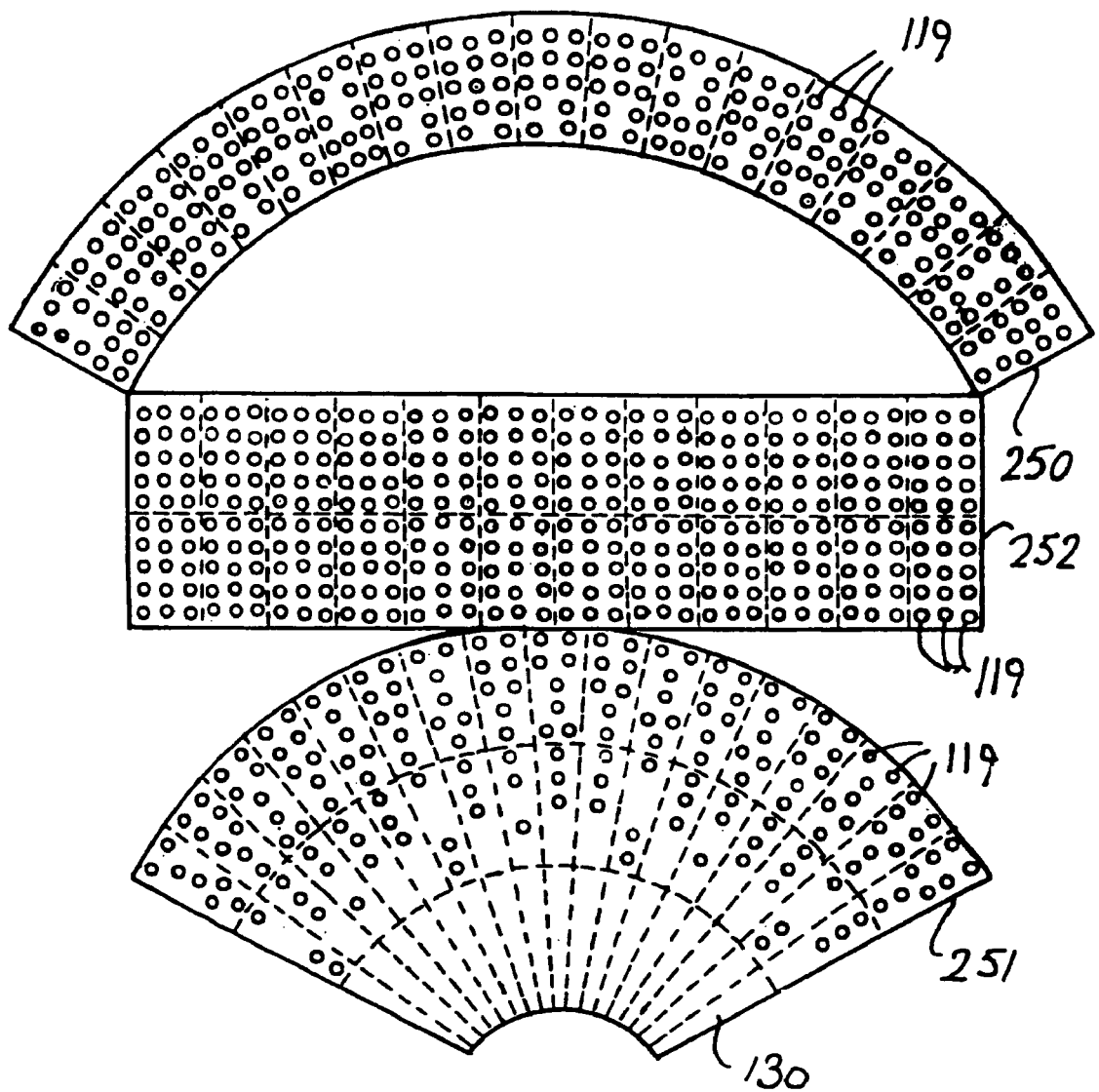
FIG. 16 is a developed view of the distal end of the filter body of FIG. 15 illustrating an arrangement of outlet holes.

Referring in particular to FIGS. 7, 8 and especially 14 (a) to 14 (e) we have found that the overall porosity of the filter element is preferably between 5% and 40% and ideally between 8% and 21%. The transverse cross sectional areas of the filter body at longitudinally spaced-apart locations of the distal portion are substantially the same. Most importantly we have found that the porosity of the distal portion of the filter body should decrease towards the distal end. Arrangements of distal holes 119 for different filter diameters are shown in FIGS. 14 (*a*) to 14 (*e*). FIG. 14 (*a*) shows an arrangement for a 6 mm filter, 14 (*b*) for a 4 mm filter, FIG. 14 (*c*) for a 4.5 mm filter, FIG. 14 (*d*) for a 5 mm filter and FIG. 14 (*e*) for a 5.5 mm filter. The number of outlet holes 119 also increases towards an outer edge of the distal portion of the filter body.

In addition we have found that for optimum capture of embolic material while facilitating retrieval of the filter with entrapped embolic material into a retrieval catheter the distal portion of the filter element includes a blind section 130 adjacent the distal end of the filter element. Ideally the blind portion 130 extends longitudinally for at least 5% and preferably less than 30% of the length of the distal portion.

In order to reduce the profile of the filter body we have significantly reduced the thickness of the filter membrane to typically in the order of 25 microns. This reduction in thickness however means that the membrane used must have a relatively high stiffness to achieve a comparable strength. However, we have found that such an increase in stiffness results in poor memory performance and is therefore undesirable.

We have surprisingly found that by providing a filter body of laminate construction in which a membrane is coated with a coating to a thickness of from 5% to 40% of the thickness of the membrane we have been able to provide a filter body which has a low profile but which has good memory characteristics.

In particular, we have found that hydrophilic coatings and hydrogels are highly suitable coatings as they have a similar surface to the endothelial lining of a blood vessel and are not perceived by the body's immune system as foreign. This results in at least reduction and in some cases substantial elimination of platelet adhesion and fibrin build up which could otherwise occlude the filter and/or create a harmful thrombus. The coating also provide a relatively low friction surface between the filter body and the delicate endothelial lining of a vessel wall and therefore minimise the trauma and injury to a vessel wall caused by deployment of the filter body in the vasculature.

A hydrogel will absorb water swelling its volume. The swelling of the hydrogel will exert an expansion force on the membrane helping to pull it into its recovered or deployed shape.

A coating that expands on contact with blood will exert an expansion force on the membrane helping to pull it into its recovered or deployed shape.

A coating that expands when subjected to body temperature will exert an expansion force on the membrane helping to pull it into its recovered or deployed shape.

Hydrophilic coatings can be classified by their molecular structure:

Linear Hydrophilic polymers can dissolve or be dispersed in water

Cross-linked hydrophilic polymers, which include hydogels, can swell and retain water.

Hydrophilic coatings may be also synthetic or natural. Synthetic hydrophilic polymers include the following:

Poly (2-hydroxy ethyl methacrylate)—(PHEMA)
Poly (vinyl alcohol)—(PVA)
Poly (ethylene oxide)—(PEO)
Poly (carboxylic acids) including:
Poly (acrylic acid)—(PAA)
Poly (methacrylic acid)—(PMAA)
Poly (N-vinyl-2-pyrollidone)—(PNVP)
Poly (sulfonic acids), poly (acrylonitrile), poly (acrylamides)

Natural hydrophylics include:
Cellulose ethers
Collagen
Carrageenan

Commercially available hydrophylic coatings suitable for coating filter membrane include, but are not limited to the following:
Aquamer (Sky Polymers Inc.)
Phosphorylcholine (PC) (Biocompatibiles Ltd)
Surmodics (Surmodics Inc. BSI)
Hydak (Biocoat Inc)
Hydomer (Hydormer Inc)

Hydrogels as stated are cross-linked hydrophilic molecules. The molecular mobility of hydrogels is constant and extensive, giving ceaseless molecular motion, which contributes to the property of biocompatibility by inhibiting protein absorption.

The extent to which a hydrogel imparts properties of biocompatibility, wettability and lubricity is directly related to the amount of water it absorbs into its molecular matrix, which is referred to as the "degree of swelling".

$$W = [(Wsw - Wo)/Wsw] \times 100$$

Where Wsw=Weight of swollen gel
Wo=Weight of dry gel $$\text{Water uptake} = U = [(Wsw - Wo)/Wsw] \times 100$$

A typical hydrogel will absorb up to 20% of their dry weight of water. Superabsorbant hydrogels will absorb up to 2000% of their dry weight of water.

Hydrogel strength is directly related to cross link density ($\mu$) and molecular weight between cross-links (Mc).

Hydrophilic coatings may be typically applied by dipping, spraying and/or brushing. The coatings may also be applied by solution or by colloidal dispersion.

The membrane surface to be coated may be prepared by cleaning with a solvent and/or ultrasonic cleaning. Plasma or corona discharge may also be used to increase the surface energy and thus provide for better adhesion.

Alternatives to Hydrophilics include low friction fluoropolymer, i.e. PTFE & FEP coatings that are chemically inert and have low coefficients of friction, which also helps prevent adhesion of platelets.

Other coatings that rely on being chemically inert include.
Poly-para-xylylene (Paralene N, C & D) made by Novatron Limited.
Diamond like carbon.
TetraCarbon (Medisyn Technologies Ltd.).

Both diamond like carbon & tetracarbon also provide very thin hard surface layers, which help reduce the dynamic coefficient of friction for elastomers.

The coating may be typically applied by dipping, spraying and/or brushing. The coatings may also be applied by solution or colloidal dispersion.

Typically, to produce a filter according to the invention a polymeric filter membrane is first produced by machining a core of a desired shape from an inert material such as perspex. The perspex core is then dipped in a solution of a polymeric material as described above. Alternatively the membrane is formed by blow moulding. Holes are then laser machined in the dipped core. The perspex core is removed by dissolving in acetone. Residual acetone is washed out with water.

A filter frame of gold plated Nitinol is mounted on a filter carrier in the form of a polyimide tube. The filter membrane is then slid over the filter support frame to provide an uncoated filter assembly.

The filter assembly is dipped in a solvent such as propan 2-ol to clean the assembly. The cleaned assembly is then dipped in a solution of a coating material. A vacuum is applied to remove excess coating material prior to drying in an oven. The coating material is typically of Aquamer in a water/ethanol solution. The thickness of the coating is typically 2 to 10 microns.

Preferably the filter body contains regions of varying stiffness and durometer hardness. The change in filter stiffness along its geometry can be achieved by varying the material properties or by modifications to the thickness or geometry of the membrane. The change in material hardness is achieved by varying the material properties. The polymer material may be one of the following: polyamides, polyurethanes, polyesters, a polyether block amide (PEBAX), olefinic elastomer, styrenic elastomer. Ideally the filter body has a durometer of between 60 D and 70 A Shore hardness Referring to FIG. 19 there is illustrated a filter element comprising a filter body 2 according to the invention. In this case, the filter body 2 has a proximal section 3 and a distal section 4 interconnected by an intermediate section 5. Both the proximal section 3 and the distal section 4 are made from a relatively stiff grade of polyurethane material which enables a low wall thickness to be achieved, thus advantageously minimising the bulk of the filter when it is in a collapsed position so that it has a low crossing profile while at the same time providing adequate strength. The intermediate section 5 is made from a soft elastic grade of polyurethane having good shape memory characteristics which will help the filter maintain the desired expanded shape during use of the filter. This soft portion also allows one filter size to accommodate a range of vessel sizes conforming closely to the vessel wall to prevent blood and embolic material bypassing the filter.

Figure 19:
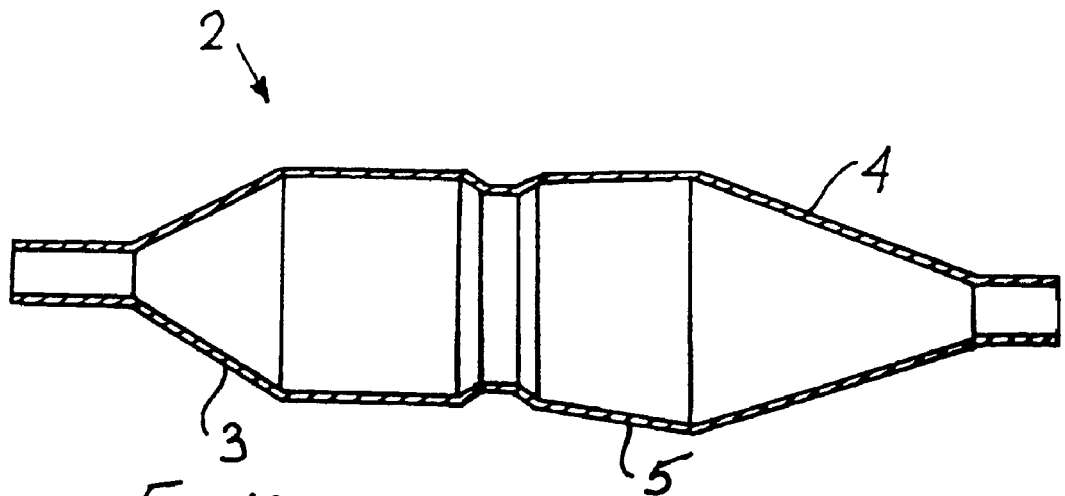
FIG. 19 is a longitudinal cross sectional view of a filter body according to the invention.
Figure 20:
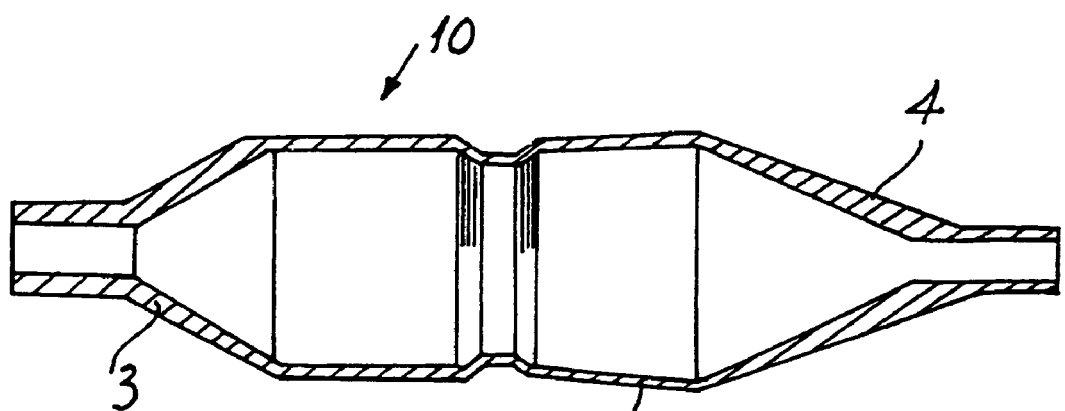

In the filter body 2 illustrated in FIG. 19 the body is of generally uniform thickness in cross section. However, to achieve any desired variation in the properties of the filter body the thickness may be variable such as in the filter body 10 illustrated in FIG. 20.

Figure 21:
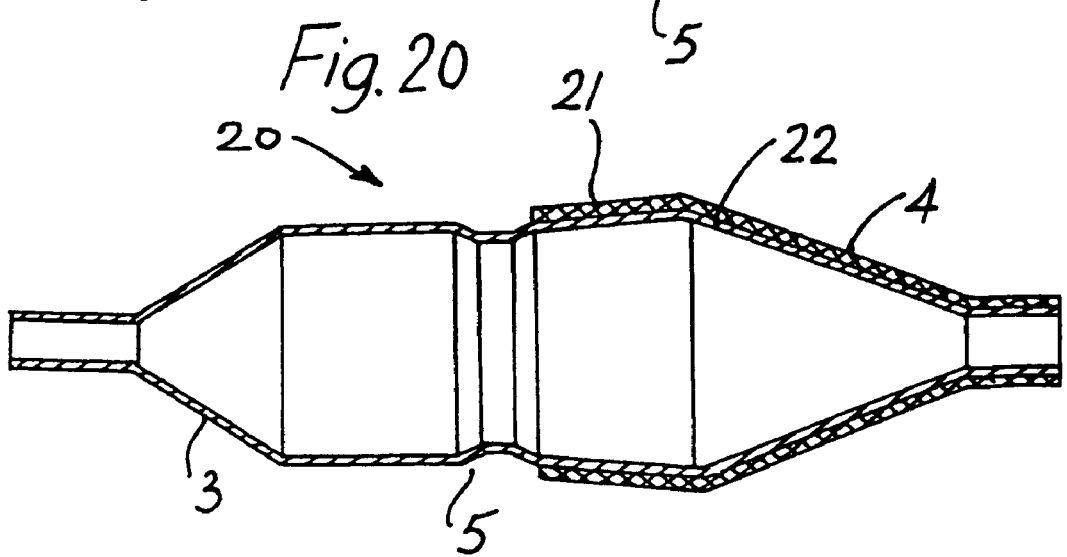

Referring to FIGS. 21 to 25, any required structural properties may also be provided by a filter body, which is at least partially of a laminate construction. The layers of the laminate may be of the same or different materials. In the illustration of FIG. 21 the distal section 4 and part of the intermediate section 5 are of a two layer 21, 22 construction. The layers 21, 22 may be of the same or different materials.

The layers 21, 22 are keyed together by mechanical or chemical means, the holes in the distal section 4 are then formed by boring through the two layers 21, 22.

In the illustration of FIG. 22 the entire filter body 30 is of a three layer 31, 32, 33 construction. Layer 31 is a structural layer made from a material such as polyether block amide (PEBAX), polyester, polyethylene, polyurethane, terephthalate (PET), or nylon. Layers 32, 33 are coating layers made from a material such as a hydrophilic, hydrogel, non-thrombogenic, or non-stick material. Layers 32, 33 may be of the same or different materials. The holes at the distal end 4 are also lined with the coating layers 32, 33.

When coating layers 32, 33 are of different materials, they are applied to structural layer 31 as follows. A temporary protective film is first sealed to the outer most surface of layer 31. Then coating layer 33 is applied to the inner most surface of layer 31 by immersing the body formed by layer 31 in a coating solution. Excess coating solution is sucked out and the protective film is removed from the outer most surface of layer 31. Another temporary protective film is then sealed to the inner most surface of layer 33. The body formed by layers 31, 33 is completely immersed in a coating solution. Excess coating solution is drawn out and the protective film is removed from the innermost surface of layer 33.

If the coating layers 32, 33 are of the same material, both layers 32, 33 may be applied to the structural layer 31 in one step without the use of protective films.

In the illustration of FIG. 23 the entire filter body 45 is of a three layer 46, 47, 48 construction. Layers 46, 47, 48 are structural layers and layers 47, 48 are of the same material. The holes at the distal end 4 are also lined with the structural layers 47, 48.

In the illustration of FIG. 24 the entire filter body 50 is of a three layer 51, 52, 53 construction. Layers 51, 52, 53 are structural layers, and in this embodiment layers 52, 53 are of different materials.

In the illustration of FIG. 25 the entire filter body 55 is of a four layer 56, 57, 58, 59 construction. Layers 56, 57 are structural layers and may be of the same or different materials. Layers 58, 59 are coating layers and may be of the same or different materials. The holes at the distal end 4 are also lined with the coating layers 58, 59.

Referring to FIG. 26 there is illustrated another filter element 60 according to the invention, which is similar to part of the distal section 4 of filter element 2 of FIG. 19. But having no proximal webbing members thus maximising the size of the inlet opening.

FIG. 27 illustrates a filter element 61, which is similar to the distal section 4 and part of the intermediate section 5 of filter element 20 of FIG. 21, having the advantages of the laminate structure previously described, combined with the large inlet opening of FIG. 26 and the variable distal geometry of FIG. 19 (enabling the filter to accommodate a range of vessel sizes).

FIG. 28 illustrates a further filter element 65, which includes a support ring 66 to maintain the intermediate section 5 open to advancing blood flow. Support ring 66 may be arranged perpendicular to the direction of the blood flow or inclined at an angle, as illustrated in FIG. 28. The support ring 66 may be of an elastic, super elastic or shape memory material, and may be either actuated remotely to appose the vessel wall in a perpendicular or close to perpendicular position, or fixed in circumference so that its inclination and shape are controlled by the diameter of the vessel.

A different layer structure may be provided at any desired location of the filter body to achieve required properties.

Figure 29:
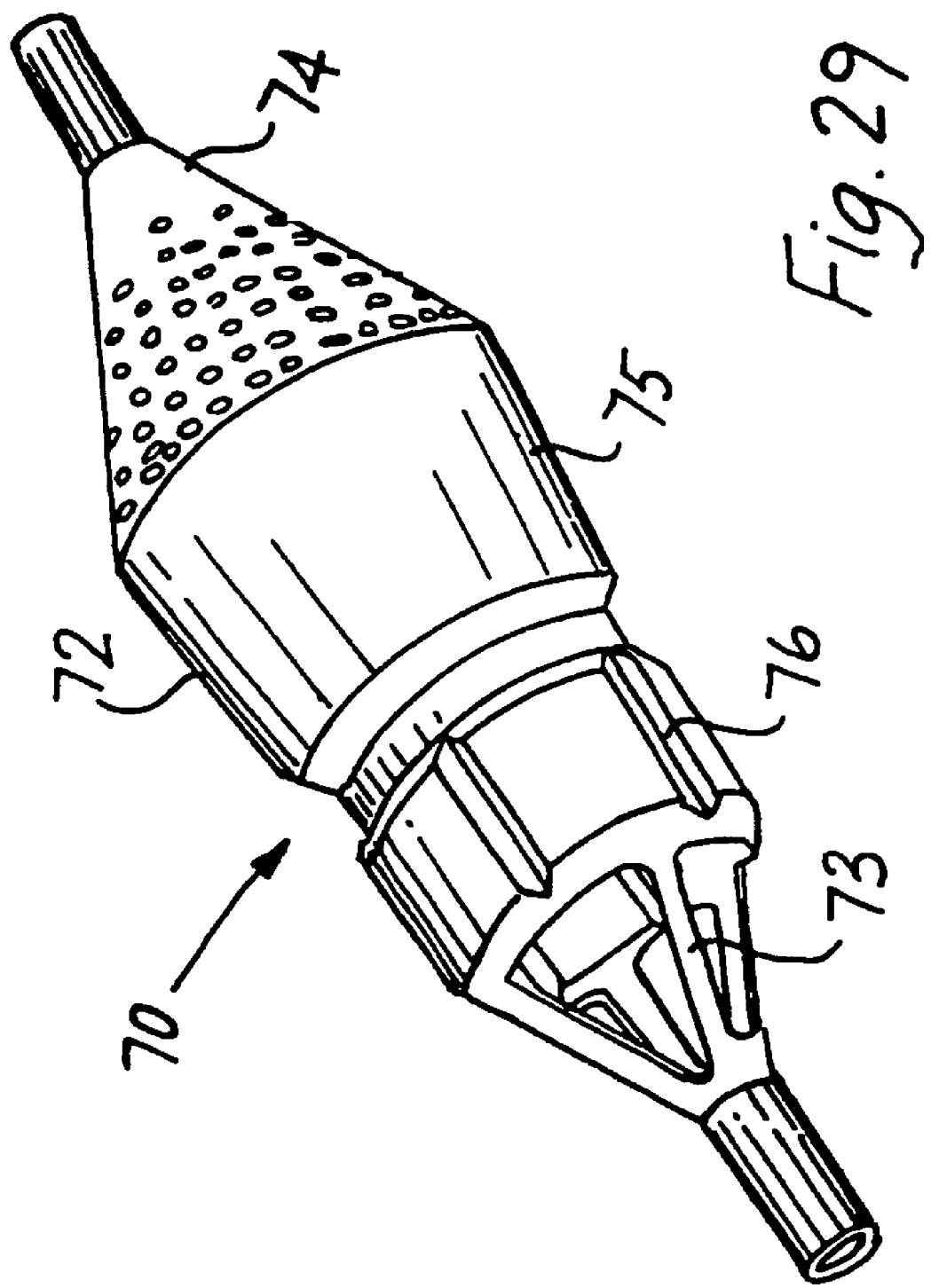
FIG. 29 is a schematic perspective view of a filter element according to another aspect of the invention.

Referring now to FIG. 29 there is shown another filter element according to the invention, indicated generally by the reference 70. The filter element 70 has a filter body 72 of generally similar construction to the filter element described previously, the body having a proximal section 73 and a distal section 74 interconnected by an intermediate section 75. In this case, the distal section 74 is of a relatively hard polyurethane material whilst the proximal section 73 and intermediate section 75 are of a softer grade polyurethane material. A number of longitudinal ribs 76 are provided around a circumference of the proximal section 73. Advantageously, this construction facilitates close engagement of an outer circumference of the proximal section 73 against a vessel wall to minimise the risk of embolic material bypassing the filter element 70. An internal support frame, as described above, urges the proximal section 73 outwardly so that it expands against and closely conforms with the wall of the blood vessel in which the filter element 70 is mounted in use.

Conveniently, the corrugations or ribs 76 allow the proximal section 73 of the filter element 70 to accommodate a wider range of vessel sizes whilst maintaining good contact between the outer circumference of the proximal section 73 and the vessel wall and providing improved filter body integrity.

Figure 30:
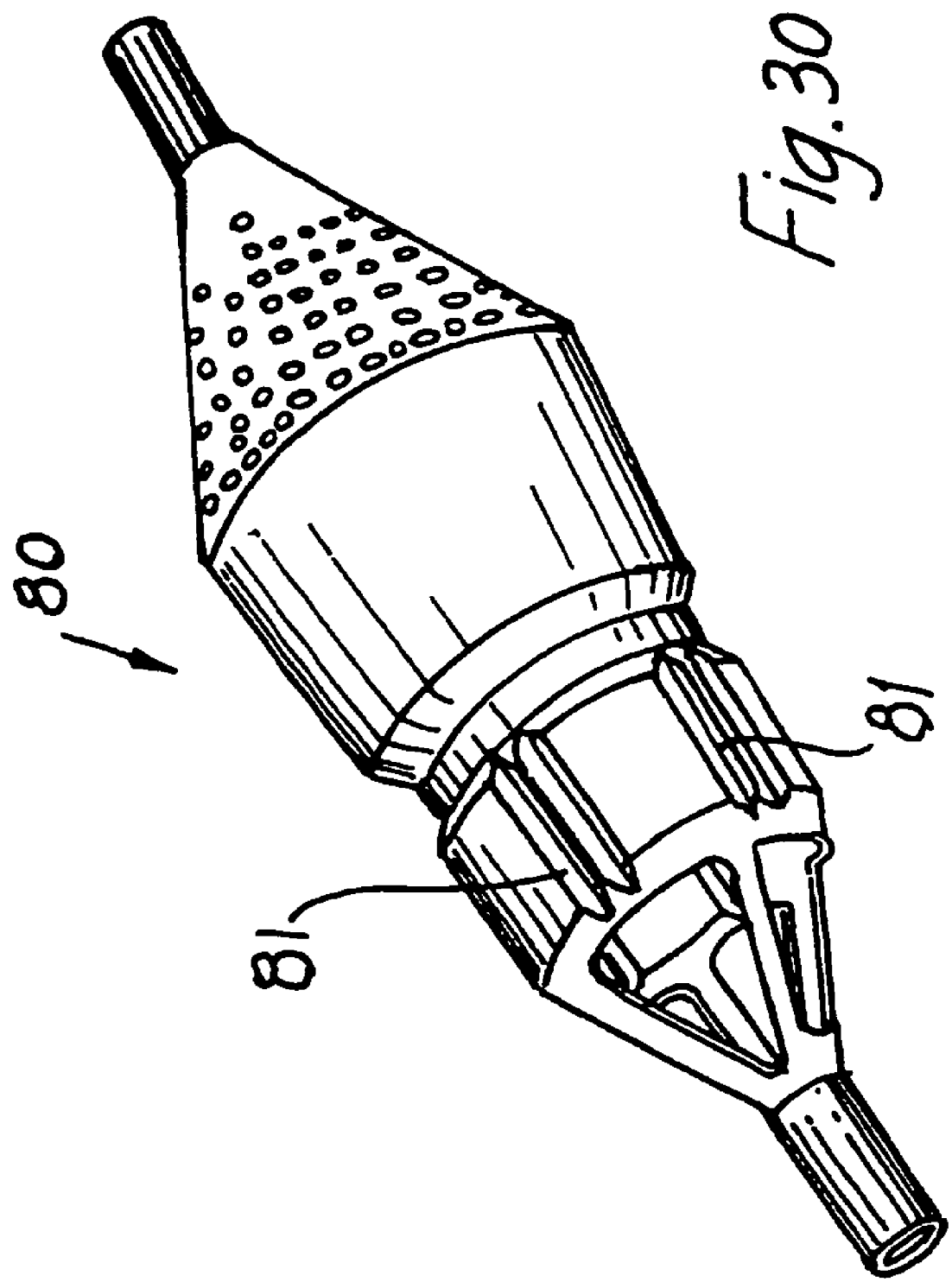
FIGS. 30 to 33 are schematic perspective views of different embodiments of the filter element according to the invention.

Referring to FIG. 30 there is illustrated another filter element 80 according to the invention. In this case corrugations 81 are provided for improved filter body integrity.

Figure 31:
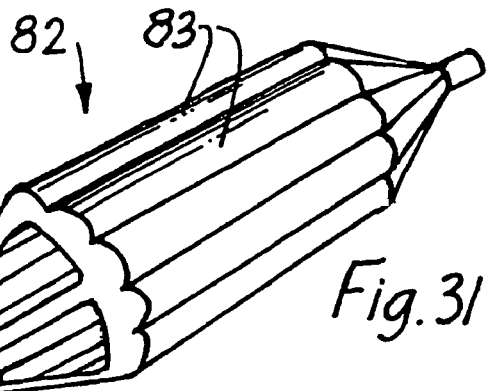

Referring to FIG. 31 there is illustrated another filter element 82 according to the invention. In this case the cross section of the filter element 82 is of a flower petal shape with a plurality of longitudinally extending ribs 83 for improved apposition. As explained in reference to FIG. 29, the "petal shaped" cross section (as for corrugations) increase the circumference of the filter body, thus enabling the body to be apposed closely against the vessel wall by a supporting structure in a wide range of vessel sizes.

Figure 32:
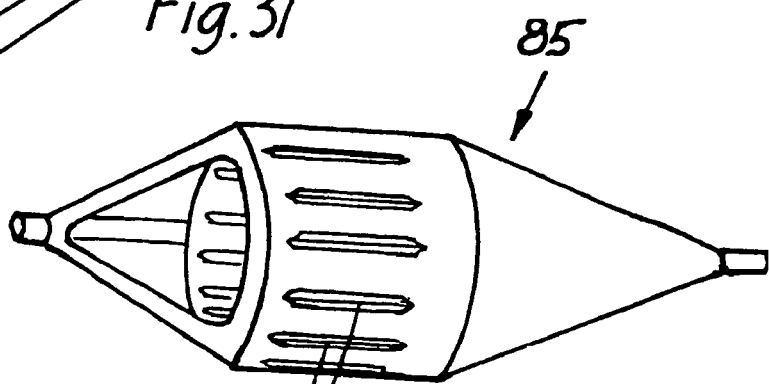

Referring to FIG. 32 there is illustrated another filter element 85 according to the invention. In this case slits 86 are provided in the place of the corrugations or "petal shapes" shown above. The slits 86 enable the body of the filter to conform to a range of vessel diamters by overlapping and preventing creasing in small diamater vessels, or allowing the body to expand with the aid of a supporting structure in larger diameter vessels. In both instances close engagement of the outer circumference with the vessel wall is facilitated, thus minimizing the risk of embolic material bypassing the filter.

Figure 33:
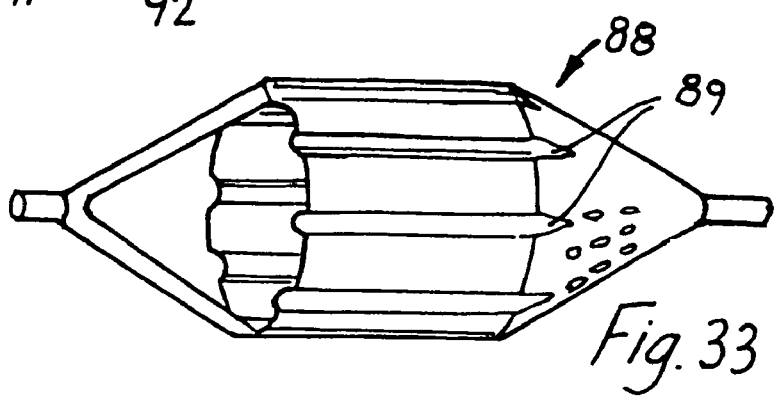

Referring to FIG. 33 there is illustrated another filter element 88 according to the invention. In this case ribs 89 are provided to prevent creases forming along the filter element 88 in the longitudinal direction, and also to allow expansion of the filter element 88.

Figure 34:
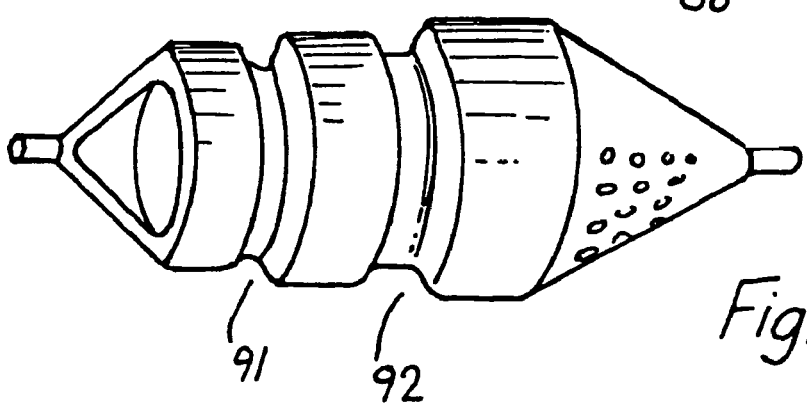
FIG. 34 is a schematic perspective view of a filter element according to a further aspect of the invention.

Referring to FIG. 34 there is illustrated a further filter element 90 according to the invention, which is of a concertina-like shape with two circumferentially extending grooves 91, 92. This circumferential grooves or ribs have several advantages. They add to the integrity of the filter body, assisting it in maintaining its shape in the vessel after deployment. They inhibit the propagation of creases between the varying diameter body segments, so that one filter can be designed for a range of vessel sizes. They enable the filter to extend in length to greatly increase its effective volume without adding to the length of the deployed device in use. This provides the benefit of safe retrieval of large embolic loads as explained with reference to stretchable membranes below.

Referring to FIGS. 35(a) to 35(d) there is illustrated another embolic protection system according to the invention incorporating a filter element 94 according to the invention which is similar to those described above. The protection system includes a guidewire 95 and a retrieval catheter 96 which is advanced over the guidewire to retrieve the filter containing trapped embolic material 97. In this case the filter body includes an intermediate 98 and distal 99 membrane, one or both of which are stretchable to facilitate the retrieval of the captured embolic material 97. The stretching of the membrane during the retrieval process is illustrated in FIGS. 35(b) to 35(d).

The use of such a stretchable filter membrane allows larger volumes of captured embolic material to be retrieved than would be possible with a stiffer membrane. This is possible because if a filter is to be retrieved by withdrawing it into or through a catheter of a given internal diameter, the maximum volume of material that can be retrieved is directly proportional to the length of the filter and the internal diameter of the catheter. The stretchable membrane allows the filter to increase in length upon retrieval, thus increasing the space available for retention of captured embolic material. This is particularly significant in the case of large volumes of captured embolic material, which will be more difficult to safely retrieve with a non-stretchable device.

The stretchable section may include some or all of the filter body, and may not necessarily include the distal cone. The distal cone containing the outlet pores may be formed from a non stretch material, while the inter mediate filter body is stretchable. This provides the advantage of filter extension during retrieval while preventing the problem of release of captured material through expanding distal pores.

Another advantage of the stretchable section is that the crossing profile can be reduced as the filter can be loaded into a delivery pod in a stretched, rather than bunched or folded, configuration. This reduces the volume of filter material contained in any given cross section of the loaded delivery pod.

In addition the use of a stretchable filter material in the intermediate section can also be advantageous by providing a section of the filter body which can be circumferentially expanded by a support frame to appose the wall of a wide range of vessel sizes.

The invention is not limited to the embodiments hereinbefore described which may be varied in detail.

The invention claimed is:

1. An embolic protection device, comprising:
a filter membrane of a polymeric material disposed over a collapsible support frame, the support frame and filter membrane at least partially movable between a collapsed position and a deployed position; and
a coating applied to the filter membrane to reduce thrombus formation in the presence of blood flowing through the embolic protection device,
wherein the filter membrane comprises at least 200 outlet openings with an average diameter of from 100 to 200 microns, and
the shear stress imparted to blood flowing through the embolic protection device at physiological flow rates is less than 800 Pa.

2. The embolic protection device according to claim 1, wherein the coating has a thickness between about 5% and 40% of the thickness of the filter membrane.

3. The embolic protection device according to claim 1, wherein the coating is a cross-linked hydrophilic polymer.

4. The embolic protection device according to claim 1, wherein the coating is a synthetic hydrophilic polymer.

5. The embolic protection device according to claim 1, wherein the coating is a natural hydrophilic polymer.

6. The embolic protection device according to claim 2, wherein the coating is a hydrogel.

7. The embolic protection device according to claim 6, wherein the hydrogel is configured to absorb water, thereby sealing the filter membrane to a body lumen.

8. The embolic protection device according to claim 1, wherein the coating is configured to mimic an endothelial lining of a membrane lumen.

9. The embolic protection device according to claim 1, wherein the coating is configured to provide a low friction surface interaction between the filter body and a wall of a body lumen.

10. The embolic protection device according to claim 1, wherein the filter membrane is treated to increase surface energy of the filter membrane prior to being coated.

11. The embolic protection device according to claim 1, wherein the filter membrane comprises a proximal portion, an intermediate portion and a distal portion, and the distal portion of the filter membrane comprises a blind section adjacent to the distal end of the distal portion, wherein the blind section extends longitudinally over 5% to 30% of the length of the distal portion of the filter membrane and there are no outlet openings in the blind section.

12. The embolic protection device according to claim 11, wherein in the deployed position, the intermediate portion is generally of a cylindrical shape and the distal portion is of a generally frusto-conical shape tapering distally inwardly.

13. The embolic protection device according to claim 11, wherein the filter membrane comprises between 200 and 1000 outlet openings.

14. The embolic protection device according to claim 11, wherein the number of outlet holes per unit area increases in the proximal direction beginning at a proximal end of the blind section.

15. The embolic protection device according to claim 1, wherein the number of outlet holes per unit area increases distally to proximally.

16. The embolic protection device according to claim 1, wherein the filter membrane has at least 800 outlet openings.

17. The embolic protection device according to claim 16, wherein the outlet holes have an average diameter of from 100 to 150 microns.

18. The embolic protection device according to claim 1, wherein the outlet holes have an average diameter of from 100 to 150 microns.

19. The embolic protection device according to claim 1, wherein the shear stress imparted to blood flowing through the embolic protection device at physiological flow rates is less than 500 Pa.

20. The embolic protection device according to claim 1, wherein the shear stress imparted to blood flowing through the embolic protection device at physiological flow rates is less than 200 Pa.

21. An embolic protection device comprising:
a collapsible filter body which is movable between a collapsed stored position for movement through a lumen and an expanded position;
a filter membrane disposed at least partially over a portion of the filter body;
a proximal inlet portion of the filter membrane having one or more inlet openings sized to allow fluid and debris to enter into the filter body and membrane;
a distal outlet portion of the filter membrane having at least 800 outlet openings with an average diameter from 100 to 150 microns formed therein to allow fluid to pass therethrough while maintaining debris within the filter membrane; and
a coating applied to the filter membrane, the coating configured to reduce shear stress on blood passing through and around the expanded filter body and membrane,
wherein the distal outlet portion of the filter membrane comprises a blind section adjacent to the distal end of the distal portion,
the blind section extends longitudinally over 5% to 30% of the length of the distal outlet portion of the filter membrane,
there are no outlet openings in the blind section, and
the shear stress imparted to blood flowing through the embolic protection device at physiological flow rates is less than 800 Pa.

22. The embolic protection device according to claim 21, wherein the coating has a thickness between about 5% and 40% of the thickness of the filter membrane.

23. The embolic protection device according to claim 21, wherein the number of outlet holes per unit area increases distally to proximally beginning at a proximal end of the blind section.

24. The embolic protection device according to claim 21, wherein the shear stress imparted to blood flowing through the embolic protection device at physiological flow rates is less than 500 Pa.

25. The embolic protection device according to claim 21, wherein the shear stress imparted to blood flowing through the embolic protection device at physiological flow rates is less than 200 Pa.

26. An embolic protection device, comprising:
a filter membrane of a polymeric material disposed over a collapsible support frame, the support frame and filter membrane movable between a collapsed position and a deployed position,
wherein the filter membrane comprises at least 200 outlet openings having an average diameter of from 100 to 150 microns, and
the shear stress imparted to blood flowing through the embolic protection device at physiological flow rates is less than 200 Pa.

* * * * *